US008348882B2

(12) United States Patent
Bardy

(10) Patent No.: US 8,348,882 B2
(45) Date of Patent: *Jan. 8, 2013

(54) INSTRUMENT WITH A COVERED BORE FOR SUBCUTANEOUS IMPLANTATION

(75) Inventor: Gust H. Bardy, Carnation, WA (US)

(73) Assignee: Cardiac Science Corporation, Bothell, WA (US)

( * ) Notice: Subject to any disclaimer, the term of this patent is extended or adjusted under 35 U.S.C. 154(b) by 30 days.

This patent is subject to a terminal disclaimer.

(21) Appl. No.: 12/836,535

(22) Filed: Jul. 14, 2010

(65) Prior Publication Data

US 2010/0324579 A1  Dec. 23, 2010

Related U.S. Application Data

(63) Continuation-in-part of application No. 12/815,364, filed on Jun. 14, 2010, which is a continuation of application No. 11/484,084, filed on Jul. 10, 2006, now Pat. No. 7,736,330, which is a continuation-in-part of application No. 11/345,617, filed on Feb. 1, 2006, now Pat. No. 7,780,625, which is a continuation of application No. 11/025,770, filed on Dec. 20, 2004, now abandoned, which is a continuation of application No. 10/222,719, filed on Aug. 15, 2002, now abandoned, which is a continuation of application No. 09/644,666, filed on Aug. 24, 2000, now Pat. No. 6,436,068.

(51) Int. Cl.
  *A61M 31/00* (2006.01)
(52) U.S. Cl. ............... 604/57; 604/59; 604/60
(58) Field of Classification Search ............ 604/57–64, 604/117, 158, 164.01, 164.04, 164.06, 164.08, 604/274; 600/432, 567

See application file for complete search history.

(56) References Cited

U.S. PATENT DOCUMENTS

| | | | |
|---|---|---|---|
| 2,513,014 A | 6/1950 | Fields | |
| 2,830,587 A | 4/1958 | Everett | |
| 3,477,437 A * | 11/1969 | Goldberg | 604/117 |
| 3,545,443 A | 12/1970 | Ansari | |
| 4,447,223 A | 5/1984 | Kaye et al. | |
| 4,531,938 A | 7/1985 | Kaye et al. | |
| D295,318 S | 4/1988 | Gazale | |
| 4,769,011 A | 9/1988 | Swaniger | |
| D301,378 S | 5/1989 | Shippert | |
| 4,832,687 A | 5/1989 | Smith, III | |
| 4,900,304 A | 2/1990 | Fujioka et al. | |
| 4,909,250 A | 3/1990 | Smith | |
| 4,915,686 A | 4/1990 | Frederick | |
| 4,936,827 A | 6/1990 | Grimm et al. | |

(Continued)

FOREIGN PATENT DOCUMENTS

FR 2 835 436 8/2003

(Continued)

*Primary Examiner* — Nicholas Lucchesi
*Assistant Examiner* — Nathan R Price
(74) *Attorney, Agent, or Firm* — Patrick J. S. Inouye

(57) ABSTRACT

An instrument with a covered bore for subcutaneous implantation is provided. An incising body defines a non-circular coaxial bore and includes a sharpened cutting edge that extends from a bottom distal end beyond the opening of the coaxial bore and an attachment point at a top distal end. A plunger is non-fixedly contained within the coaxial bore and slides longitudinally therein. A cover is pivotally attached at the attachment point and extends down to the bottom distal end and, when closed, the cover encloses the opening proximal to the cutting edge.

18 Claims, 18 Drawing Sheets

U.S. PATENT DOCUMENTS

| | | | |
|---|---|---|---|
| 4,941,874 A | 7/1990 | Sandow et al. |
| 4,950,234 A | 8/1990 | Fujioka et al. |
| 5,250,026 A | 10/1993 | Ehrlich et al. |
| 5,273,532 A | 12/1993 | Niezink et al. |
| 5,279,554 A | 1/1994 | Turley |
| 5,279,555 A | 1/1994 | Lifshey |
| 5,284,479 A | 2/1994 | De Jong |
| 5,300,106 A | 4/1994 | Dahl et al. |
| 5,304,119 A | 4/1994 | Balaban et al. |
| 5,331,966 A | 7/1994 | Bennett et al. |
| 5,358,474 A | 10/1994 | Kaldany |
| 5,405,324 A | 4/1995 | Wiegerinck |
| 5,484,403 A | 1/1996 | Yoakum et al. |
| 5,501,664 A | 3/1996 | Kaldany |
| 5,501,672 A | 3/1996 | Firth et al. |
| 5,507,807 A | 4/1996 | Shippert |
| 5,526,772 A | 6/1996 | Curkendall |
| 5,558,637 A | 9/1996 | Allonen et al. |
| 5,562,613 A | 10/1996 | Kaldany |
| 5,669,890 A | 9/1997 | Grimm |
| 5,772,671 A | 6/1998 | Harmon |
| D396,287 S | 7/1998 | Morales |
| 5,810,769 A | 9/1998 | Schlegel et al. |
| 5,827,293 A | 10/1998 | Elliott |
| 5,908,404 A | 6/1999 | Elliott |
| 5,944,732 A | 8/1999 | Raulerson et al. |
| 5,984,890 A | 11/1999 | Gast et al. |
| 6,190,350 B1 | 2/2001 | Davis et al. |
| 6,230,059 B1 | 5/2001 | Duffin |
| 6,245,052 B1 | 6/2001 | Orth et al. |
| 6,261,243 B1 | 7/2001 | Burney et al. |
| 6,293,925 B1 | 9/2001 | Safabash et al. |
| 6,317,626 B1 | 11/2001 | Warman |
| 6,488,649 B1 | 12/2002 | Lichten |
| 6,551,289 B1 | 4/2003 | Higuchi et al. |
| 6,682,480 B1 | 1/2004 | Habib et al. |
| 6,761,725 B1 | 7/2004 | Grayzel et al. |
| 7,247,160 B2 | 7/2007 | Seiler et al. |
| D593,201 S | 5/2009 | Lash et al. |
| 7,942,843 B2 | 5/2011 | Tune et al. |
| 2003/0135153 A1 | 7/2003 | Hagemeier |
| 2004/0082969 A1* | 4/2004 | Kerr ............... 606/205 |
| 2005/0216028 A1* | 9/2005 | Hart et al. ............ 606/108 |
| 2009/0018603 A1 | 1/2009 | Mitelberg et al. |

FOREIGN PATENT DOCUMENTS

| | | |
|---|---|---|
| WO | PCT/GB99/02389 | 7/1999 |
| WO | PCT/GB99/02393 | 7/1999 |
| WO | PCT/US99/08353 | 10/1999 |

\* cited by examiner

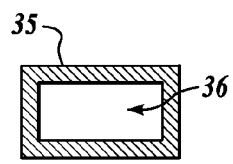
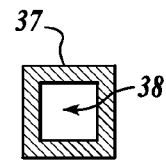
FIG.5A    FIG.5B
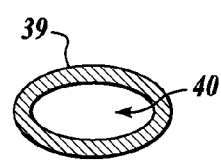
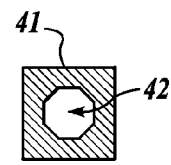
FIG.5C    FIG.5D
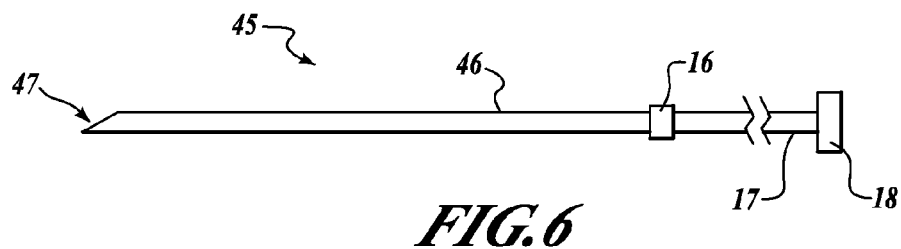
FIG.6
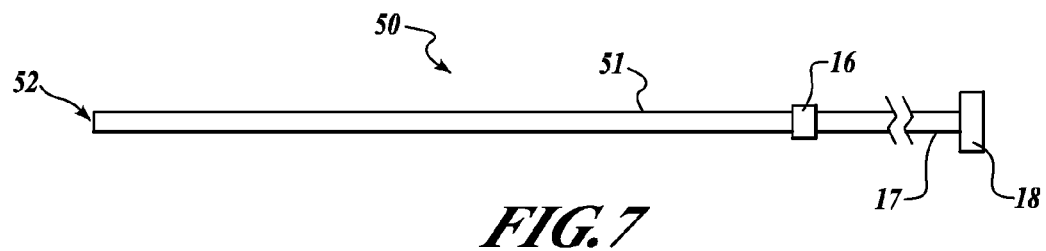
FIG.7

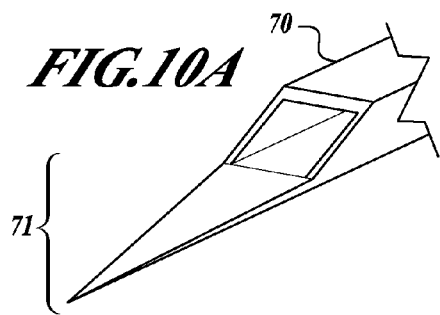
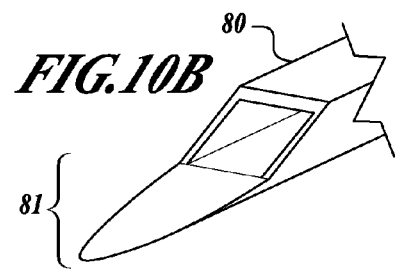
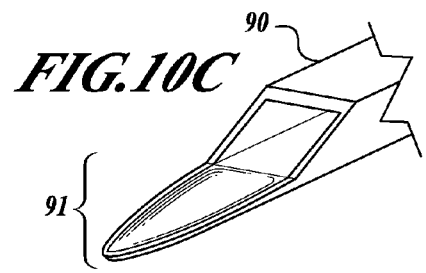
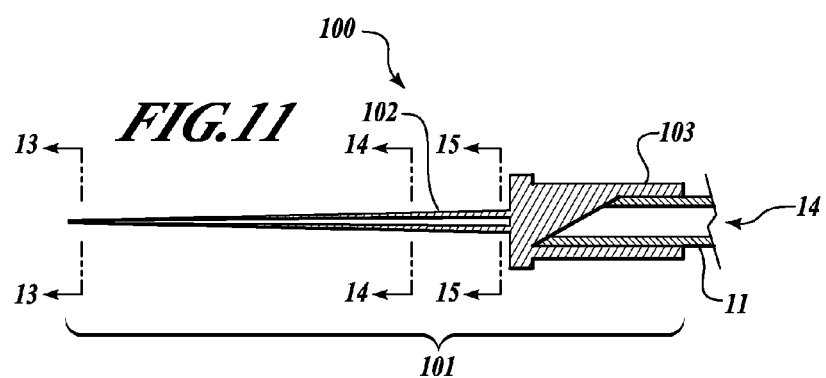
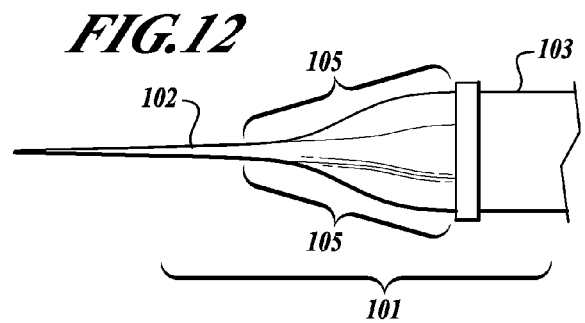

○ *FIG.13*

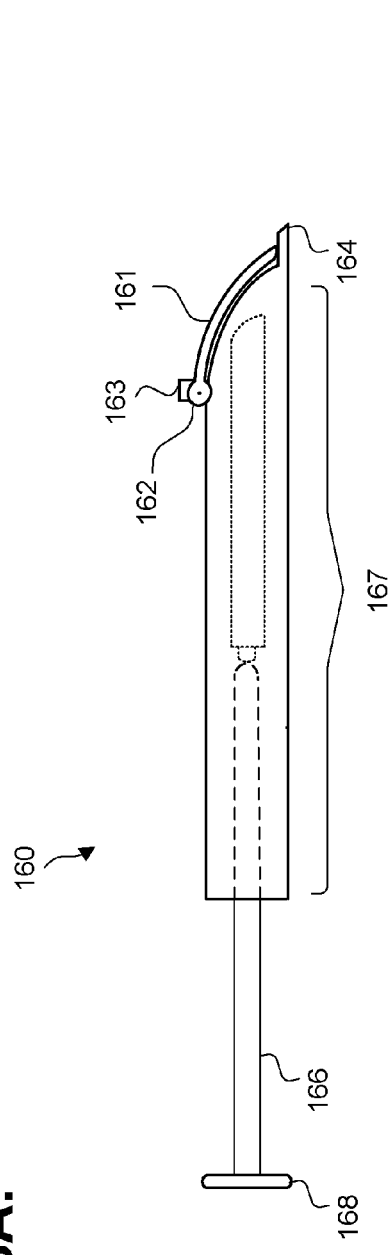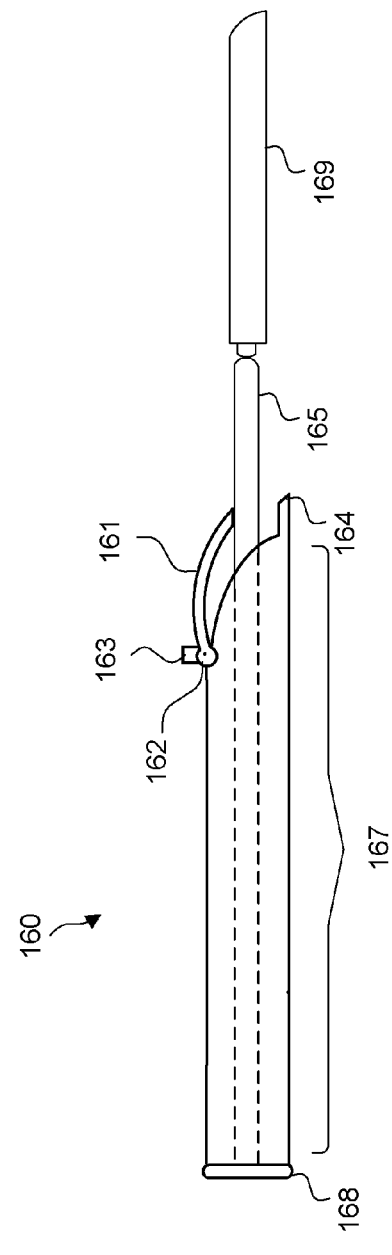
Fig. 23A.
Fig. 23B.

INSTRUMENT WITH A COVERED BORE FOR SUBCUTANEOUS IMPLANTATION

CROSS-REFERENCE TO RELATED APPLICATIONS

This patent application is a continuation-in part of U.S. patent application, Ser. No. 12/815,364, filed Jun. 14, 2010, pending; which is a continuation application of Ser. No. 11/484,084, filed Jul. 10, 2006, now U.S. Pat. No. 7,736,330, issued Jun. 15, 2010; which is a continuation-in-part of Ser. No. 11/345,617, filed Feb. 1, 2006, now U.S. Pat. No. 7,780,625, issued Aug. 24, 2010; which is a continuation of U.S. patent application Ser. No. 11/025,770, filed Dec. 20, 2004, abandoned; which is a continuation of U.S. patent application Ser. No. 10/222,719, filed Aug. 15, 2002, abandoned; which is a continuation of Ser. No. 09/644,666, filed Aug. 24, 2000, now U.S. Pat. No. 6,436,068, issued Aug. 20, 2002, the priority dates of which are claimed and the disclosures of which are incorporated by reference.

FIELD

The present invention relates in general to subcutaneous implantation instruments and, in particular, to an instrument with a covered bore subcutaneous implantation.

BACKGROUND

Health care assessment includes the review and analysis of physiometry collected and recorded by electronic data sensors. The type and quality of physiometry can depend upon the type and location of sensor used. External sensors, such as thermometers, blood pressure cuffs, heart rate monitors, and the like, are limited in the kinds of information, which they are able to collect, and can encumber the patient. Implantable in situ sensors can provide a direct stream of recorded physiometry, but are invasive and require surgical implantation.

Recent advances in microchip technology have created a new generation of highly integrated, implantable monitors, sensors and medical devices, such as implantable cardioverter defibrillators, pacemakers, and insertable loop recorders. For instance, PCT Publication Nos. WO/2000/004945, to Habib et al., published Feb. 3, 2000, and WO/2000/004946, to Habib et al., published Feb. 3, 2000, respectively describe an implantable sensor chip and treatment regiment, the disclosures of which are incorporated by reference. Each sensor chip can collect and transmit physiometric data by wireless telemetry to a receiver external to a body. Similarly, the emerging Bluetooth wireless communication standard, described at http://www.bluetooth.com/developer/specification/specification.asp, proposes a low cost, small form factor solution for short range data communications, potentially suitable for use in implantable sensor technology.

Nevertheless, microchip sensors must still be implanted via some form of surgical procedure with the need to provide a sterile field, surgical staff, and surgical risks. Minimally invasive implantation using large bore needles or flat-edged blades is impracticable because sensors, particularly when embodied using microchip technology, favor a prismatic shape with substantially rectangular cross sections that are incompatible with circular bores.

As well, large bore needles can core out flesh, skin, or hide, when used in animals, as the instruments are inserted subcutaneously, which creates a risk of injury, scarring, and infection. Additionally, cored flesh trapped within the needle's bore can clog or interfere with correct implant placement. Moreover, wider-tipped instruments, such as a hollow point chisel, can potentially cause tearing, gouging, or similar injury around the implant site due to the width of the cutting edge.

In addition, although current surgical implantation approaches attempt to minimize the size of incision and degree of invasiveness, implantation is, at best, costly, time-consuming, traumatic, requires multiple instruments and maneuvers, and potentially risky to the patient. For example, anesthetizing is conventionally performed using a topical or local anesthetic agent on the implantation site.

Subcutaneous implantable sensors offer the best compromise between in situ sensors and external sensors and are potentially insertable with a simple injection, rather than surgical procedure. These sensors are typically implanted below the dermis in the layer of subcutaneous fat. Several approaches to the subcutaneous implantation of solid materials have been described.

An insertion and tunneling tool for a subcutaneous wire patch electrode is described in U.S. Pat. No. 5,300,106, to Dahl et al., issued Apr. 5, 1994. The tunneling tool includes a stylet and a peel-away sheath. The tunneling tool is inserted into an incision and the stylet is withdrawn once the tunneling tool reaches a desired position. An electrode segment is inserted into the subcutaneous tunnel and the peel-away sheath is removed. Although providing a tool for subcutaneous implantation, the Dahl device requires an incision into the subcutaneous fat layer and forms an implantation site larger than the minimum sized required by the electrode segment. Furthermore, the tunneling tool slices a tunnel through the tissue from the skin's surface all the way to the site of implantation, which creates a deep and infection-susceptible wound.

An implant system for animal identification that includes a device for implanting an identification pellet in a fat layer beneath the hide or skin of an animal is described in U.S. Pat. No. 4,909,250, to Smith, issued Mar. 20, 1990. The device includes a curved needle-like tube that terminates at a tapered, sharpened point. An elongated, flexible plunger is slidably received within the needle-like tube. The pointed tip is inserted through the hide or skin and the plunger is actuated to drive the identification pellet from the tip into the fat layer. However, the Smith device uses an oversized open bore, which can cause coring of the hide or flesh.

A trocar for inserting implants is described in PCT Publication No. WO/1999/053991, to Peery, published Oct. 28, 1999. An implant retention trocar includes a cannula for puncturing the skin of an animal and an obturator for delivering the implant. A spring element received within the cannula prevents an implant from falling out during the implant process. The cannula has a distal tip design, which is limited to cannulas having a circular bore and thereby limits the size and shape of implant.

An instrument for injecting implants through animal hide is described in U.S. Pat. No. 5,304,119, to Balaban et al., issued Apr. 19, 1994. The instrument includes an injector having a tubular body divided into two adjacent segments with a hollow interior bore. A pair of laterally adjacent tines extend longitudinally from the first segment to the distal end of the tubular body. A plunger rod has an exterior diameter just slightly larger than the interior diameter of the tubular body. With the second segment inserted beneath the animal hide, the push rod is advanced longitudinally through the tubular body, thereby pushing the implant through the bore. As the implant and rod pass through the second segment, the tines are forced radially away from each other, thereby dilating or expanding the incision, and facilitating implant. The instrument forms an implantation site larger than minimally necessary, leading to an increased chance of collateral trauma to the site.

Therefore, there is need for a non-surgical instrument and method for subcutaneous implantation of sensors and solid materials that preferably does not require an incision preparatory to instrument insertion.

There is a further need for a subcutaneous implantation instrument and method capable of implanting sensors and other solid materials that are not readily disposed to implantation through a substantially circular bore.

Moreover, there is a further need for a subcutaneous implantation instrument and method which is minimally invasive, preferably creating the smallest needed implantation site, and capable of implantation without exposing the implant to longitudinal stresses.

There is a still further need for an implantation instrument that provides a progressive widening of an implantation site. Such progressive widening would facilitate the use of wider-tipped instruments that provide sufficient girth to admit implantable sensors and medical devices with lowered patient trauma. Preferably, such an instrument would include provision for application of an anesthetic agent.

There is a still further need for an implantation instrument that reduces the risk of coring of, or other injury to, tissue during implant site dissection and the amount of additional trauma to the surrounding tissue.

SUMMARY

An implantation instrument and method of use for implanting sensors and other solid materials in a subcutaneous or other site is provided. As used herein, "subcutaneous" refers generally to those implantation sites located within a body below the skin The implantation instrument consists of an incising shaft attached to a syringe body. The syringe body and incising shaft both define a substantially non-circular hollow bore for accommodating the sensor or solid material. The subcutaneous site is formed by a cutting edge on the distal end of the incising shaft. The subcutaneous site can be cleared using a clearing trocar slidably received within the hollow bore. The sensor or solid material is advanced through the hollow bore and delivered into the subcutaneous site. The depth of the subcutaneous site can be limited using a penetration limiting mechanism.

One embodiment provides an instrument with a covered bore for subcutaneous implantation. An incising body defines a non-circular coaxial bore and includes a sharpened cutting edge that extends from a bottom distal end beyond the opening of the coaxial bore and an attachment point at a top distal end. A plunger is non-fixedly contained within the coaxial bore and slides longitudinally therein. A cover is pivotally attached at the attachment point and extends down to the bottom distal end and, when closed, the cover encloses the opening proximal to the cutting edge.

A further embodiment provides an instrument with a hinged cover for subcutaneous implantation. An incising body defines a non-circular coaxial bore and includes a sharpened cutting edge extending from a bottom distal end beyond the opening of the coaxial bore and an attachment point at a top distal end. A plunger is non-fixedly contained within the coaxial bore and slides longitudinally therein. A cover is pivotally attached by a hinge at the attachment point and extends down to the bottom distal end and, when closed, the cover encloses the opening proximal to the cutting edge.

A further embodiment provides an instrument with a unitary cover for subcutaneous implantation. An incising assembly includes an incising body that defines a non-circular coaxial bore and a sharpened cutting edge that extends from a bottom distal end beyond the opening of the coaxial bore and an attachment point at a top distal end. A cover is integrally formed with the incising body and is pivotally attached at the attachment point and extends down to the bottom distal end and, when closed, the cover encloses the opening proximal to the cutting edge. A plunger is non-fixedly contained within the coaxial bore and slides longitudinally therein.

A further embodiment provides an instrument with a captive plunger for subcutaneous implantation. An incising body includes an incising shaft that defines a cavity located along a longitudinal axis and a sharpened cutting edge that extends from a bottom distal end beyond the opening of the cavity and an attachment point at a top distal end. A syringe body defines a bore extending along the longitudinal axis and includes a circumference smaller than the cavity, the syringe body is positioned on a proximal end of the incising shaft with the bore aligned with a portion of the cavity. A plunger assembly includes a plunger shaft sized to fit within the syringe body and is affixed on one end to a plunger including a captive member and that is sized to fit in the cavity. A cover pivotally attaches at the attachment point and extends down to the bottom distal end and, when closed, the cover encloses the opening of the cavity proximal to the cutting edge.

One principal value of such a subcutaneous implantation instrument and method would be to enable the subcutaneous insertion of implantable objects and devices, such as sensors, without an operating room or special procedures room. In essence, the subcutaneous implantation instrument and method reduce insertion of implantable objects and devices having non-conforming shapes to be the functional equivalent of an injection.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIGS. 5A-D are transverse cross-sectional views of the implantation instrument illustrating, by way of example, various bore configurations;

FIG. 6 is a segmented side view of a clearing trocar;

FIG. 7 is a segmented side view of a pushing stylet; and

FIGS. 10A-10C are perspective views of cutting edges formed on distal edges of incising shafts, in accordance with further embodiments;

FIG. 11 is a longitudinal cross-sectional view of a subcutaneous implantation instrument in accordance with a further embodiment;

FIG. 12 is a top plan view of the subcutaneous implantation instrument of FIG. 11;

FIGS. 13-15 are transverse cross-sectional views of the dissecting tool assembly of FIG. 11;

FIG. 23A is a side view of an implantation instrument with a curved cover in a closed position, in accordance with a further embodiment;

FIG. 23B is a side view of the implantation instrument of FIG. 23A with the cover in an open position;

DETAILED DESCRIPTION

Figure 1:
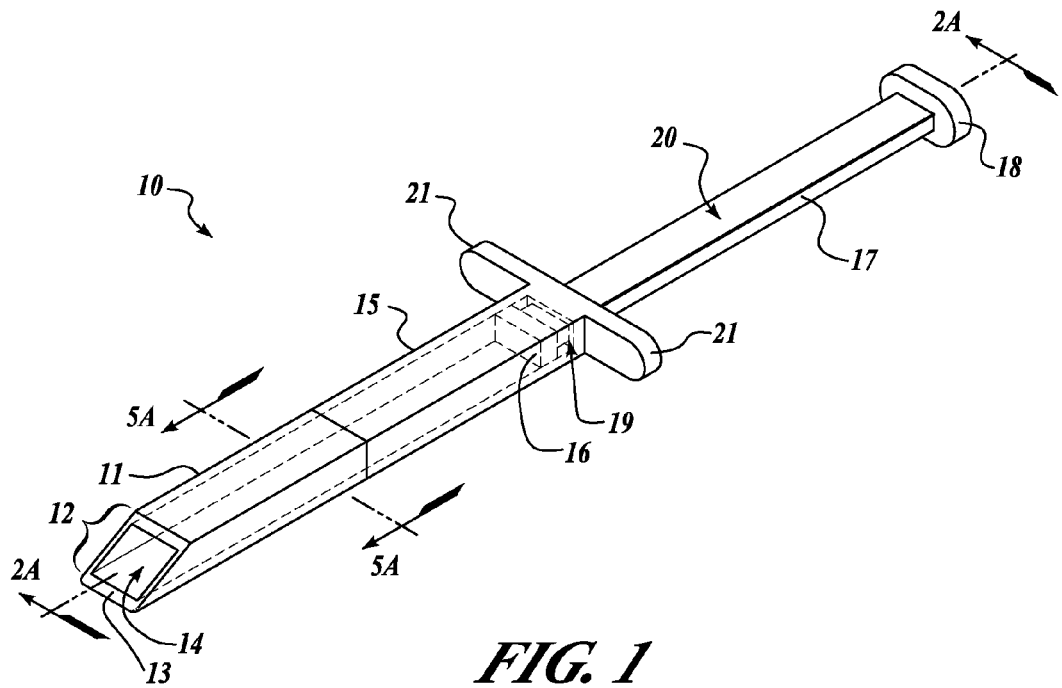
FIG. 1 is a perspective view of an instrument for implanting sensors or solid materials in a subcutaneous or other tissue location in accordance with the present invention.

FIG. 1 is a perspective view of an instrument 10 for implanting objects in a subcutaneous or other tissue location in accordance with the present invention. The implantation instrument 10 consists of two principal groups of components, an incising body consisting of an incising shaft 11 and a syringe body 15, and a delivery assembly consisting of a plunger assembly 20. The instrument 10 can be used to non-surgically implant an object, such as a sensor or monitor, medical therapeutic device, or other solid or semi-solid object. The delivery assembly is received into the syringe body bore by sliding the plunger assembly 20 through proximal bore opening 19. An implantable object is received into the syringe body bore. During an implant procedure, the implantable object is deployed into the incising shaft and thence inserted subcutaneously into an implantation site by progressive distal urging of the plunger assembly 20, as further described below beginning with reference to FIG. 18.

The incising shaft 11 is a hollow point chisel that is formed with a beveled and rounded tip 12 that tapers into a surgically sharpened cutting edge 13 formed on a distal edge. The beveled tip 12 includes a distal bore opening 14 through which the implantable object is delivered into the implantation site.

The implantable object includes medical monitoring and diagnostic devices, such as an implantable physiometry sensor, and non-medical monitoring devices, such as an environmental or activity monitor. Such sensors generally record data for subsequent retrieval and can be autonomously triggered or triggered manually by the implant recipient. One implantable sensor microchip suitable for use in the present invention is described in PCT Publication No. WO/2000/004945, to Habib et al., published Feb. 3, 2000, the disclosure of which is incorporated by reference. Such a sensor could be used for monitoring and collecting physiological or chemical measures. A further implantable monitoring device suitable for use is the Reveal insertable loop recorder, manufactured by Medtronic, Inc., Minneapolis, Minn., which is an implantable heart monitor for diagnosing the causes of syncope and other transient heart symptoms involving rhythm-related disorders, as described in U.S. Pat. No. 5,331,966, issued Jul. 26, 1994 to Bennett et al; U.S. Pat. No. 6,230,059, issued May 8, 2001 to Duffin; and U.S. Pat. No. 6,317,626, issued Nov. 13, 2001 to Warman, the disclosures of which are incorporated by reference. Other medical monitoring and diagnostic devices are possible.

The implantable object also includes non-sensor-type implantable medical devices, including implantable medical devices for therapeutic uses, such as administering cardiac pacing or rhythm therapy; providing neural, muscle, or organ stimulation; cancer treatment; and delivering or dosing medication. As well, the present invention has equal applicability to implantation of other types of non-medical sensors, including location and identification sensors, such as radio frequency identification (RFID) tags. Such sensors could include data transmitters with which to exchange recorded data and instructional signals.

Finally, the implantable object can include solid or semi-solid materials, such as a gelatinous drug bolus. In one embodiment, the implantable object has approximate dimensions of 5 mm by 10 mm by 20 mm, although other dimensions can be equally suitable. The critical dimension is the cross-sectional profile, that is, the height and width, of the implant, which must conform to passage through the syringe body and incising shaft bores. Other non-linear, prismatic shapes are equally usable provided the implantable object can fit within the confines of the syringe body and incising shaft bores. The implant could also be folded or compacted to minimize the cross-sectional profile with the implant unfolding or expanding upon implantation. As well, the implant is preferably protected against damage by encasement within, for example, a mannitol pellet in the case of a solid drug delivery system or epoxy in the case of an implantable sensor or medical device. Other sizes, shapes, and types of non-liquid implantable objects are possible.

The incising shaft 11 is fixably attached to the syringe body 15 through frictional, adhesive, or preformed constructive means, as is known in the art. Both the incising shaft 11 and syringe body 15 define a substantially non-circular hollow bore extending continuously along a shared longitudinal axis, as further described below with reference to FIGS. 5A-D.

The plunger assembly includes a plunger 16, an interconnecting plunger shaft 17 and a plunger end piece 18. The plunger 16 is conformably shaped to fit within the syringe body bore. The plunger end piece 18 facilitates deployment of the plunger assembly through the syringe body bore and is preferably shaped to fit a thumb or palm impression. In a further embodiment, the non-circular hollow bore opens to the distal end of the incising shaft 11 and extends only partly through to thereby form a cavity, rather than a tube, but with provision for the sliding of the plunger shaft 17.

In the described embodiment, the implantation instrument 10 is designed for inexpensive and disposable use utilizing low-cost, sanitizable materials. The implantation instrument 10 can be used for out-patient or non-surgical subcutaneous implant and insertion of an implantable object, as further described below beginning with reference to FIG. 18. The incising shaft 11 can be fashioned from surgical grade stainless steel and has the approximate dimensions of approximately 10 mm by 5 mm in cross section. The incising shaft 11 is approximately 50 mm long and the length can be varied to accommodate different implantation depths. The plunger 16 is formed from plastic and rubber and preferably forms a watertight seal within the syringe body bore and has the approximate dimensions of approximately 8 mm by 3 mm in cross section. The plunger shaft 17 and plunger end piece 18 are formed from plastic or similar material. Other materials, as would be recognized by one skilled in the art, could be substituted.

In a further embodiment, the syringe body 15 and plunger assembly can be replaced by an automated injection system, such as used with immunization injection guns or similar devices. These devices typically employ compressed air or other inert gases to administer medication in lieu of manual plungers. Other automated variations include spring-loaded and similar mechanical injection systems. The incising shaft 11 is fixably attached to the automated injection system which functions as a delivery mechanism in place of the syringe body 15 and plunger assembly. Thus, the implant would be pushed through the incising shaft bore using the compressed air or gas, or mechanical equivalent.

Figure 21:
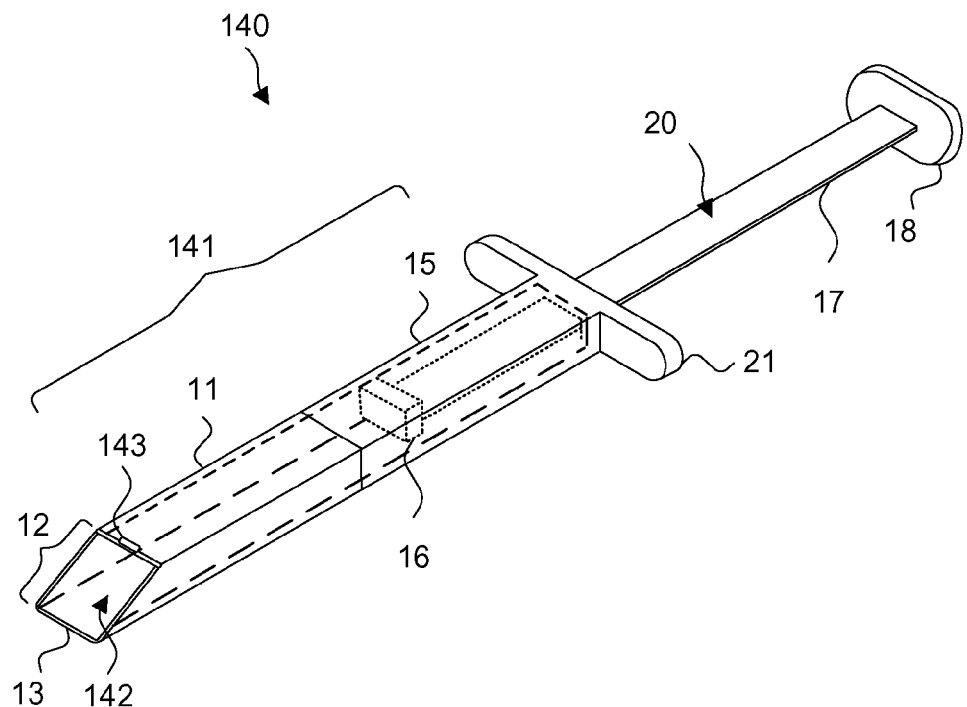
FIG. 21 is a perspective view of an implantation instrument with a covered bore, in accordance with a further embodiment.

In a yet further embodiment, the distal bore opening 14 can be enclosed by a cover attached to the top of the end of the incising body, as further described below beginning with reference to FIG. 21.

Figure 2A:
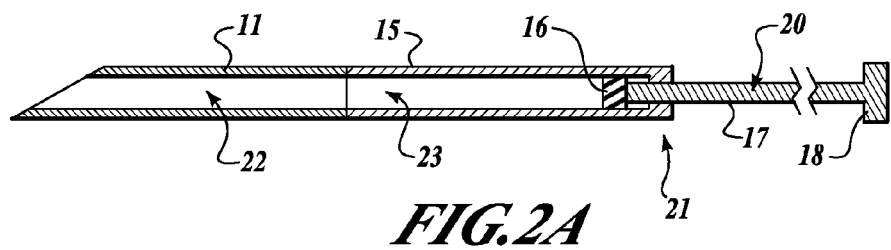
FIG. 2A is a longitudinal cross-sectional view of the implantation instrument with a straight incising shaft.

FIG. 2A is a longitudinal cross-sectional view of the implantation instrument 10 with a straight incising shaft 11. The hollow bore defined by both the incising shaft 11 and the syringe body 15 runs along a common shared axis. The incising shaft bore 22 is sized to allow the implant to advance smoothly into the implantation site under the forward lateral urging of the plunger assembly 20. The syringe body bore 23 must be at least as large as the incising shaft bore 22, but can be slightly larger to accommodate lubricants, anesthetizing agents, or similar coatings, such as mannitol, applied over the implantable object.

The syringe body 15 preferably includes a circular collar 21, pair of winglets, ears, or eyelets, or similar structure, optionally formed on a proximal end of the syringe body 15 to assist a user in depressing the plunger assembly 20.

Figure 2B:
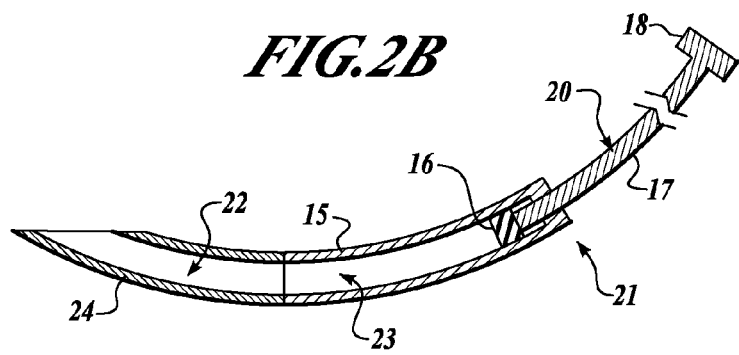
FIG. 2B is a longitudinal cross-sectional view of the implantation instrument with a curved incising shaft.

FIG. 2B is a longitudinal cross-sectional view of the implantation instrument with a curved incising shaft 24. The curved incising shaft 24, as well as the syringe body 15 and related components, are shaped into a substantially continuous curve along the ventral side. The curvature helps regulate the penetration depth of the incising shaft and, in the described embodiment, has an arc of approximately 20 degrees.

Figure 3:
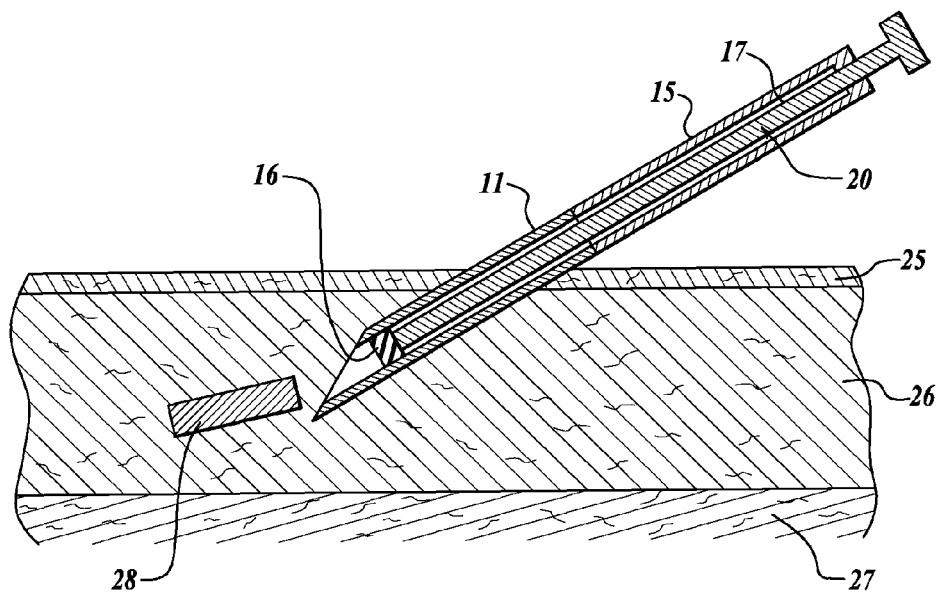
FIG. 3 is a diagrammatic view illustrating the implantation of an object into a subcutaneous site.

FIG. 3 is a diagrammatic view illustrating the implantation of an implantable object 28, including a sensor, implantable medical device, such as an implantable cardioverter defibrillator, pacemaker, or insertable loop recorder, or other solid material into a subcutaneous site. Other implantable objects are possible. During implantation, the incising shaft 11 is inserted through the dermis 25 and guided into the layer of subcutaneous fat 26, above the layer of muscle 27, to a subcutaneous implantation site. The implantable object 28 is fed through the proximal bore opening 19 or received through the distal bore opening of the syringe body 15. The implantable object 28 is then further advanced through the syringe body bore 23 and the incising shaft bore 22 by the plunger 16 into the subcutaneous site. Note that although the foregoing view illustrates an implant into the subcutaneous fat layer, one skilled in the art would appreciate that subcutaneous implantation locations are not strictly limited to the subcutaneous fat layer and are generally termed as those implantation locations situated subdurally within a body under the skin Accordingly, subcutaneous implantation sites further include locations that are intramuscular and submuscular, or within a body cavity, including intrathoracic.

In a further embodiment, the implantable object 27 is enclosed within the incising body at the distal end by a cover. The implantable object is delivered to the implantation site through the cover, as further described below with reference to FIGS. 22 and 24A-C.

Figure 4A:
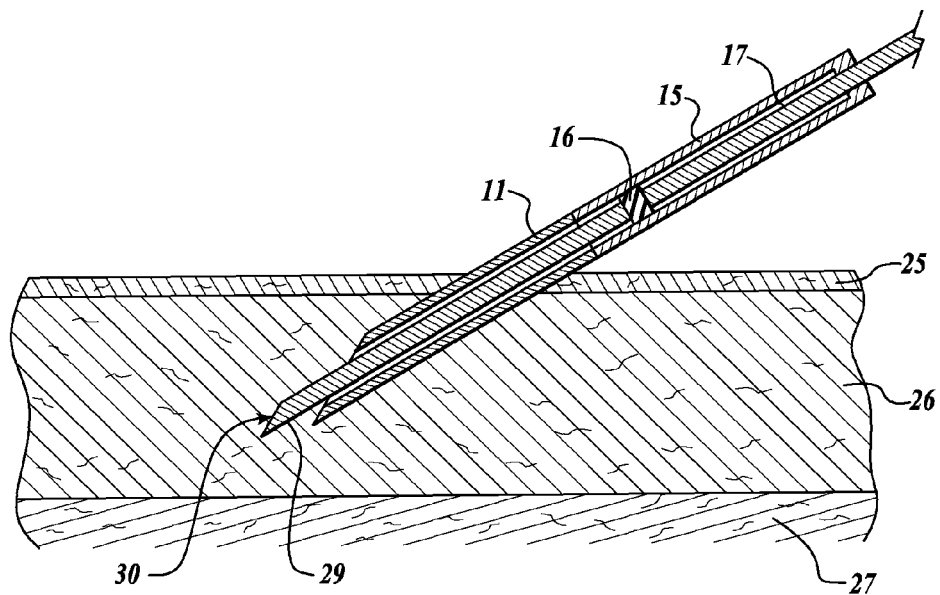
FIG. 4A is a diagrammatic view illustrating the clearing of a subcutaneous site using the implantation instrument fitted with a clearing trocar in accordance with a further embodiment.

FIG. 4A is a diagrammatic view illustrating the clearing of a subcutaneous site using the implantation instrument 10 fitted with a clearing trocar 29 in accordance with a further embodiment. The clearing trocar 29, as further described below with reference to FIG. 6, is mounted to its own handle or plunger assembly and has a sharpened cutting tip 30 for optionally clearing a subcutaneous site prior to delivery of the implant.

Prior to implantation, the clearing trocar 29 is slidably received into the syringe body 15 and is advanced until the cutting tip 30 is even with the proximal bore opening 19 of the incising shaft 11. During operation, the incising shaft 11 and clearing trocar 29 are inserted through the dermis 25 and guided into the layer of subcutaneous fat 26, above the layer of muscle 27.

The cutting edge 13 of the beveled tip 12 makes an entry incision through the dermis 25 and is laterally pushed into the subcutaneous fat 26 until the cutting edge 13 is adjacent to the subcutaneous site. The clearing trocar 29 is then urged through the subcutaneous fat 26 by advancement of its handle or plunger assembly to prepare the implantation site for delivery of the implantable object 28, including an implantable sensor, medical device, or other solid material. The clearing trocar 29 is then withdrawn from the subcutaneous site and out of the implantation instrument 10.

Figure 4B:
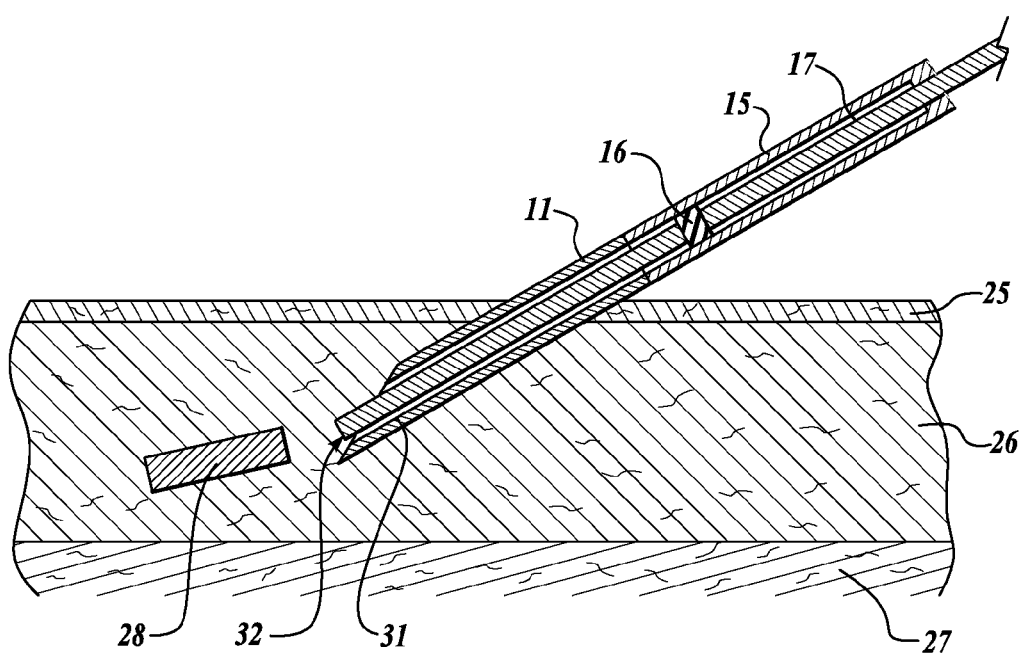
FIG. 4B is a diagrammatic view illustrating the subcutaneous implantation of an object using the implantation instrument fitted with a pushing stylet in accordance with a further embodiment.

FIG. 4B is a diagrammatic view illustrating the subcutaneous implantation of an implantable object 28 using the implantation instrument 10 fitted with a pushing stylet 31 in accordance with a further embodiment. The pushing stylet 31, as further described below with reference to FIG. 7, has a blunt tip 32 for advancing the implantable object 28 through the syringe body bore 23 and incising shaft bore 22 and into the subcutaneous site. The cross section of the pushing stylet 31 closely conforms to the incising shaft bore 22 while the plunger 16 closely conforms to the syringe body bore 23. The pushing stylet 31 thus extends the reach of the plunger assembly 20 and allows the syringe body bore 23 to have a different cross-section than the incising shaft bore 22.

The pushing stylet 31 is used while the incising shaft 11 is in situ in the subcutaneous layer 26. Prior to delivery, the implantable object 28 is fed through the proximal bore opening 19 of the syringe body 15 and further advanced within the syringe body bore 23 by contact with the plunger 16. The pushing stylet 31 is slidably received into the syringe body 15 and is advanced until the blunt tip 32 contacts the implantable object 28. During operation, the implantable object 28 is urged through the incising shaft bore 22 by the pushing stylet 31 and into the subcutaneous site by advancement of the plunger assembly. Upon delivery of the implantable object 28 into the subcutaneous site, the incising shaft 11 and pushing stylet 31 are withdrawn.

Although operation of the implantation instrument 10 is described with reference to the implantation of sensors or solid materials into a subcutaneous site situated within the layer of subcutaneous fat 26, implantations could also be effected in other subcutaneous, intramuscular, intraperitoneal, intrathoracic, intracranial, intrajoint, as well as other organ or non-subcutaneous sites, as would be recognized by one skilled in the art. In addition, the foregoing procedure could be modified to forego the use of the clearing trocar 29 for small implantable objects 28. The clearing effect of the clearing trocar 29 can be approximated by use of the incising shaft 11 alone whereby the incising shaft 11 is inserted into the subcutaneous site and then withdrawn by reverse deployment, thereby forming a slightly overwide implantation site.

The operations of subcutaneous implantation can be carried out over a plurality of sites and with the same or different implantable objects 28. Similarly, several implantable object 28 could be implanted at the same subcutaneous site during a single implantation operation.

FIGS. 5A-D are transverse cross-sectional views of the implantation instrument 10 illustrating, by way of example, various bore configurations. FIG. 5A illustrates an incising shaft 35 with a substantially rectangular bore 36. FIG. 5B illustrates an incising shaft 37 with a substantially square bore 38. FIG. 5C illustrates an incising shaft 39 with a substantially oval bore 40. And FIG. 5D illustrates an incising shaft 41 with a substantially hexagonal bore 42. Note the circumferential shape of the incising shaft need not follow the internal shape of the incising shaft bore. Other bore configurations, including variations on oval, rectangular, square, pentagonal, hexagonal, heptagonal, octagonal, and similar equilateral or nonequilateral shapes, are feasible.

In the described embodiment, the rectangular bore 36 has the dimensions of approximately 10 mm by 5 mm. The syringe body bore 23 has a length of approximately 5 cm.

FIG. 6 is a segmented side view of a clearing trocar 45. The clearing trocar 45 consists of a beveled tip 47 on the distal end of the clearing trocar 45 and a clearing trocar shaft 46 affixed, either fixably or removably, to the distal end of a plunger 16.

During a clearing operation, the clearing trocar 45 is fully extended from the distal bore opening 14 of the incising shaft 11. The clearing trocar shaft 46 is only long enough to clear out the subcutaneous site. The plunger 16 acts as a stop that limits the extent of penetration of the clearing trocar 45, thereby preventing the clearing trocar 29 from incising too deeply into the subcutaneous fat 29. In addition, the clearing trocar 29 is sized to approximate the girth of the incising shaft bore 22 and will clear a subcutaneous site only as wide as minimally necessary to facilitate implantation of the implantable object. In the described embodiment, the clearing trocar 45 has a length of approximately 2 cm beyond the tip of the syringe body 15.

FIG. 7 is a segmented side view of a pushing stylet 50. The pushing stylet 50 consists of a blunt tip 52 on the distal end of the pushing stylet 50 and a pushing stylet shaft 51 affixed, either fixably or removably, to the distal end of a plunger 16.

During a delivery operation, the pushing stylet 50 is extended from the distal bore opening 14 of the incising shaft 11. The pushing stylet shaft 51 is only long enough to clear the distal bore opening 14. The plunger 16 acts as a stop that limits the lateral travel of the pushing stylet 50. In the described embodiment, the pushing stylet 50 has an additional length of approximately 2 cm beyond the tip of the syringe body 15.

Figure 8A:
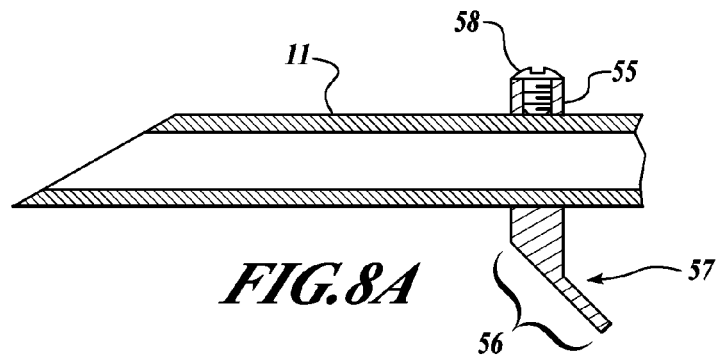
FIGS. 8A-8B are section views illustrating penetration limiting mechanisms for use with the implantation instrument.
Figure 8B:
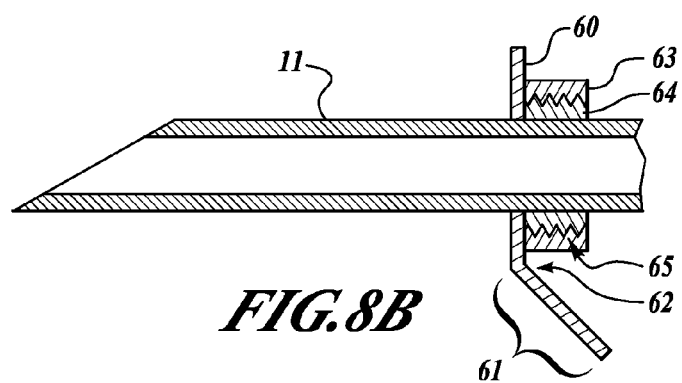

FIGS. 8A-8B are section views illustrating penetration limiting mechanisms for use with the implantation instrument 10. The penetration limiting mechanisms limit the depth of penetration of the incising shaft 11 and help prevent excessive penetration. FIG. 8A shows a fixed penetration limiting mechanism consisting of a stopping flange 55 attached to the incising shaft 11. The position of the stopping flange 55 along the incising shaft 11 can be adjusted by loosening a hold-down screw 58 and sliding the stopping flange 55 into the desired location. The lower edge of the stopping flange 55 has a bend 57 with an angle T, preferably between approximately 30° and 60°, thereby forming an elbow 56 which stops lateral travel upon contact with the skin.

FIG. 8B shows an adjustable penetration limiting mechanism consisting of a stopping flange 60 attached a frictional collar 64. The stopping flange 60 and frictional collar 64 are slidably attached to the incising shaft 11. An adjustable collar 64, preferably in threaded communication 65 with the frictional collar 64, manually stops deployment of the penetration limiting mechanism by tightening the frictional collar 64 against the incising shaft 11. The lower edge of the stopping flange 60 has a bend 62 with an angle v, preferably between approximately 30° and 60°, thereby forming an elbow 61 which stops lateral travel upon contact with the skin.

Figure 9:
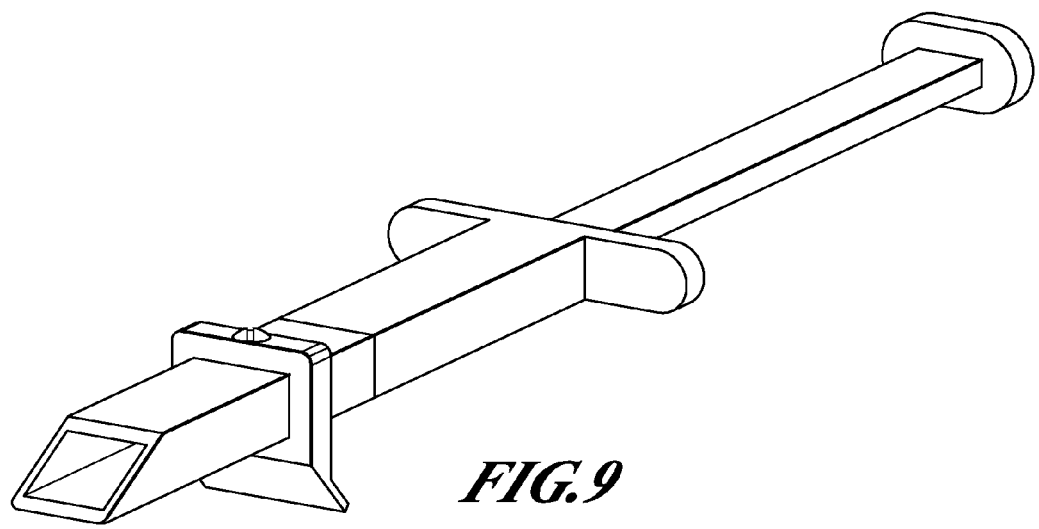
FIG. 9 is a perspective view of an instrument for implanting objects in a subcutaneous or other tissue location in accordance with a further embodiment of the present invention.

FIG. 9 is a perspective view of an instrument for implanting objects in a subcutaneous or other tissue location in accordance with a further embodiment of the present invention. The instrument is equipped with the stopping flange 55 shown in FIG. 8A. Other forms of penetration limiting mechanisms, both fixed and adjustable, could be used, as would be readily apparent to one skilled in the art.

In addition to being flat and chisel-like, the cutting edge of the incising shaft can be shaped as a progressive cutting or clearing blade, or a dissecting tool suitable for use in facilitating subcutaneous insertion. FIGS. 10A-10C are perspective views of progressive cutting edges 71, 81, 91 formed on distal edges of incising shafts 70, 80, 90 in accordance with further embodiments. The cutting edge can be shaped to facilitate subcutaneous insertion, such as when necessary to penetrate areas of thick epidermis, for instance, on the hands or feet, or animal hide. For instance, the cutting edge 71 can be shaped into a point or semi-point, which can initially pierce and progressively enlarge an implantation site. Similarly, the cutting edge 81 can be shaped into a rounded or curved edge, which can also progressively enlarge an implantation site, but without initial piercing. In addition, the cutting edge 91 upwardly curved or angled, which can help shape the implantation site to more closely follow the contours of the object to be implanted. Other cutting edge shapes are possible. Moreover, dissecting tools could be used in addition to or in lieu of the progressive cutting edges, such as a flat or shaped dissecting tool.

FIG. 11 is a longitudinal cross-sectional view of a subcutaneous implantation instrument 100 in accordance with a further embodiment. A dissecting tool assembly 101 is removably affixed to the distal end of the incising shaft 11 with a coupling sheath 103, which can be constructed as an over sleeve frictionally fit over the incising shaft 11, a snap-off assembly that detaches from the incising shaft 11 by twisting or distal movement, or some other type of coupling that is non-integral to the incising shaft 11. The dissecting tool assembly 101 includes a needle tip 102 that defines a lumen that internally interfaces to the bore opening 14 of the incising shaft 11 and which can be used to inject a local anesthetic agent or other liquid or semi-liquid substance into the implantation site. The needle tip 102 also progressively defines a pair of cutting blades along each outward facing edge.

FIG. 12 is a top plan view of the subcutaneous implantation instrument 100 of FIG. 11. The cutting blades are oriented longitudinally and planar to the cutting edge 13 of the incising shaft 11. The cutting blades provide cutting edges 105, which gradually increase the width of the incision made when the implantation instrument 100 is inserted subcutaneously. The cutting edges 105 can be straight, concave, convex, or a combination thereof.

Figure 14:
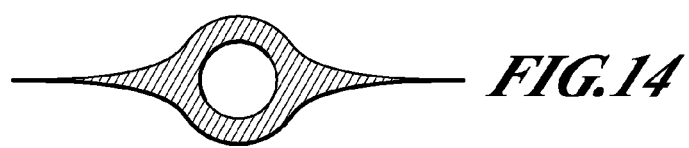
Figure 15:
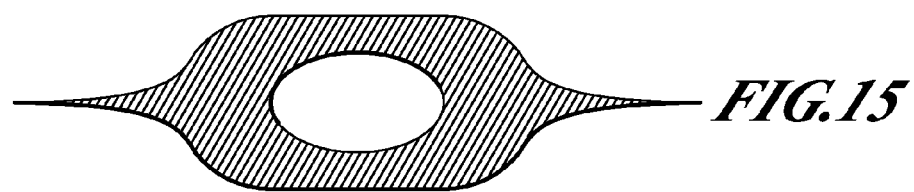

FIGS. 13-15 are transverse cross-sectional views of the dissecting tool assembly 101 of FIG. 11. On a distal end, the needle tip 102 internally defines a lumen of approximately 16 French, which tapers outwardly to a larger diameter bore and substantially non-circular bore of approximately 30 gauge on the proximal end. The cutting edges 105 become increasingly pronounced towards the proximal end of the needle tip 102. Other lumen, bore sizes, and cutting edge arrangements are possible.

Figure 16:
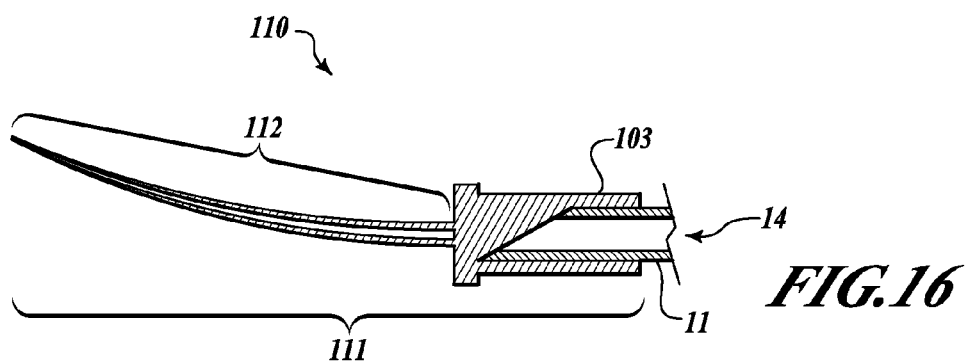
FIG. 16 is a longitudinal cross-sectional view of a subcutaneous implantation instrument in accordance with a still further embodiment.

FIG. 16 is a longitudinal cross-sectional view of a subcutaneous implantation instrument 110 in accordance with a still further embodiment. A curved dissecting tool assembly 111 bends in a gradual arc 112 upwardly towards the incising blade 11 to facilitate implantation. The curved dissecting tool assembly 111 can be used with either the straight incising shaft 11 or curved incising shaft 24. The curvature enables the implantable object to be more easily oriented parallel to the surface of the skin, rather than at an angle.

Figure 17:
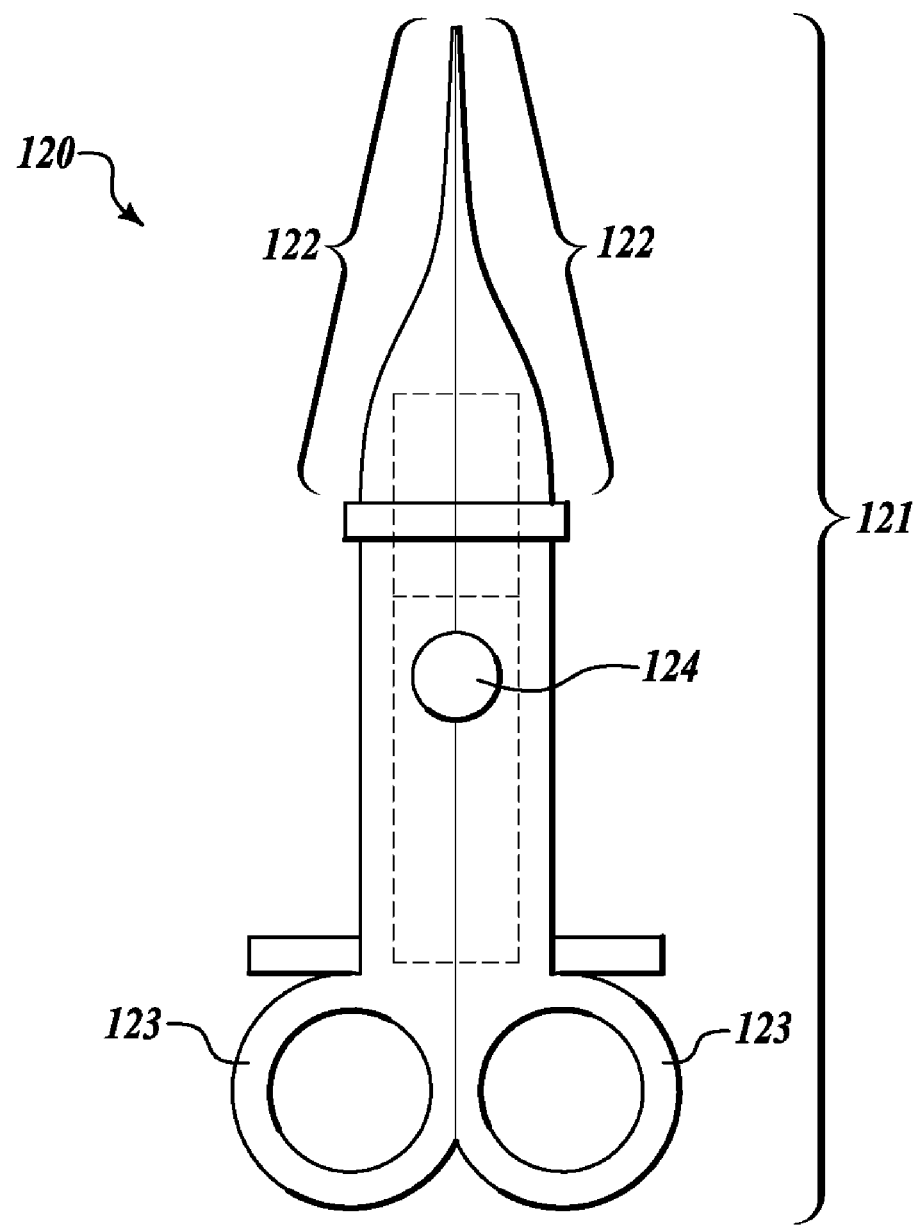
FIG. 17 is a top plan view of a subcutaneous implantation instrument in accordance with an even further embodiment.

FIG. 17 is a top plan view of a subcutaneous implantation instrument 121 in accordance with an even further embodiment. A scissored dissecting tool assembly 122 is divided into two halves, which are each attached to a handle 123 that is pivotably mounted 124, in the manner of a pair of scissors. The handles 123 can be operated outwardly to cause the distal end of the scissored dissecting tool assembly 122 to open and longitudinally cut into the surrounding tissues, thereby widening the implantation site. Once the implantation site has been suitably cleared, the scissored dissecting tool assembly 122 remains open and the plunger assembly 20 is progressive urged distally to insert the implantable object. The scissored dissecting tool assembly 122 can be straight or curved to facilitate implantation. Other forms of scissored dissecting tool assemblies are possible.

Figure 18:
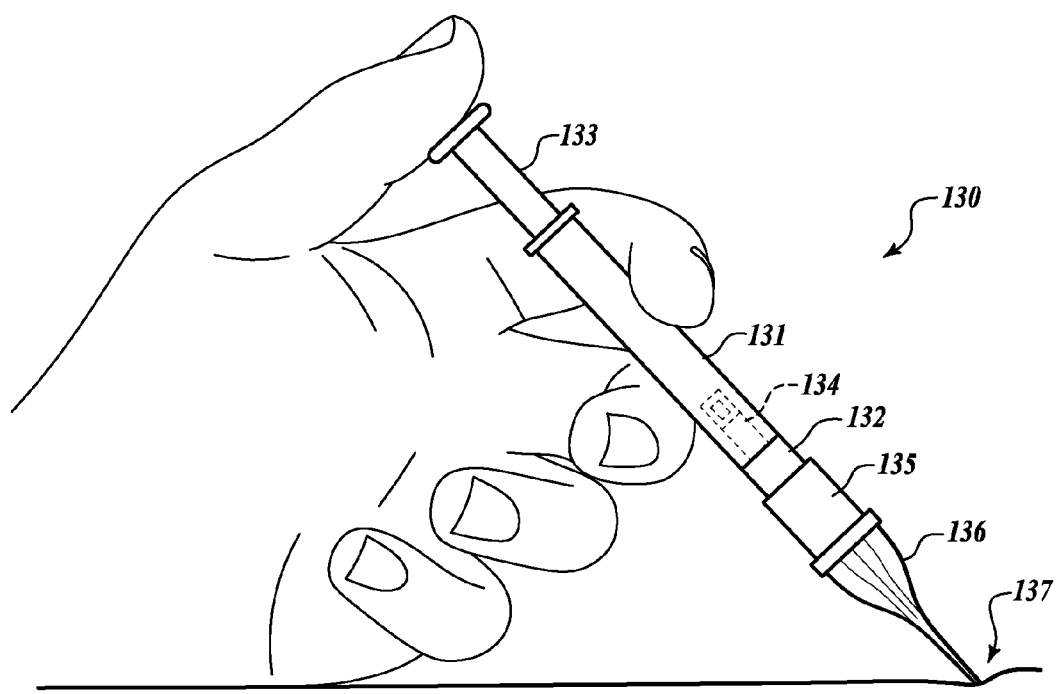
FIGS. 18-20 are perspective diagrams showing a method of use for the subcutaneous implantation instrument in accordance with one embodiment.
Figure 19:
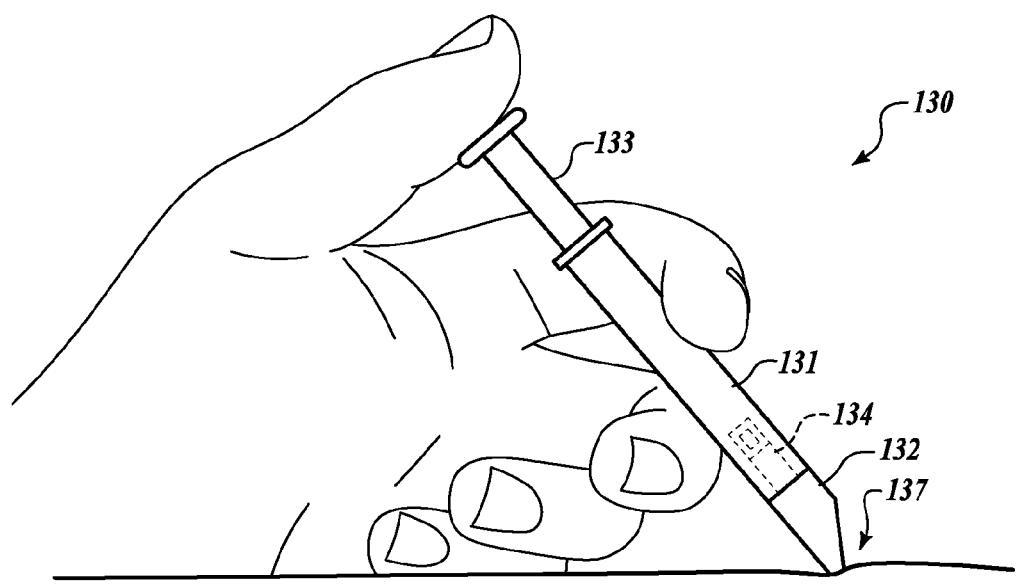
Figure 20:
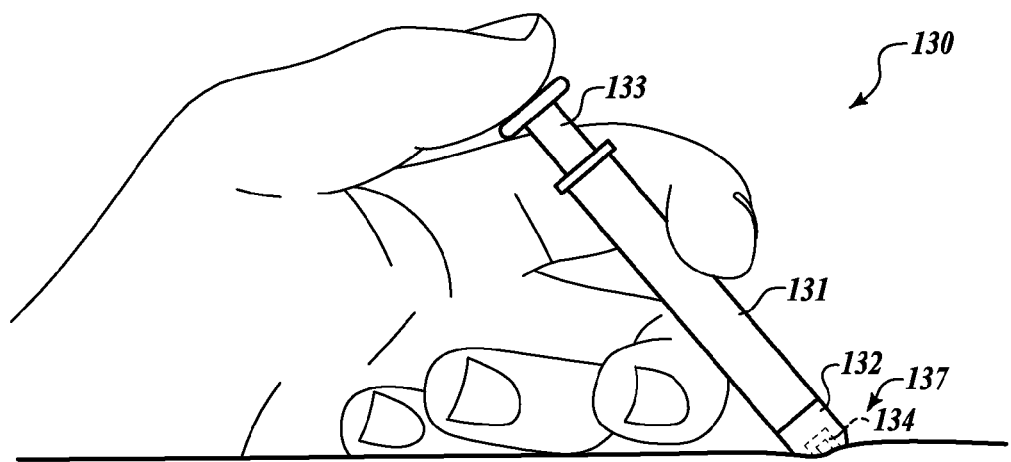

FIGS. 18-20 are perspective diagrams showing a method of use for the subcutaneous implantation instrument 121 in accordance with one embodiment. Referring first to FIG. 18, the subcutaneous implantation instrument 130 can be used for out-patient or non-surgical subcutaneous insertion of an implantable object, such as an implantable sensor, medical device, or solid material. The implantation instrument 10 enables the subcutaneous insertion of implantable objects and devices, such as sensors, without an operating room or special procedures room. The implantation instrument 10 reduce insertion of implantable objects and devices having non-conforming shapes to be the functional equivalent of an injection.

The subcutaneous implantation instrument 130 can be sold or marketed as part of a package that combines an implantable object 134 with the subcutaneous implantation instrument 130, particularly where the subcutaneous implantation instrument 130 is provided as a single-use disposable unit. Thus, the subcutaneous implantation instrument 130 can be offered with an implantable 134 object already disposed within the syringe body 131, with the entire package sealed ready for use inside sterile packaging (not shown). Alternatively, the subcutaneous implantation instrument 130 can be offered in combination with an implantable object 134 that is packaged separately.

At the outset of the procedure, an implantation site 137 can be locally anesthetized using the subcutaneous implantation instrument 130 by fitting the incising shaft 132 with a dissecting tool assembly 136, as provided in a further embodiment, described above with reference to FIG. 11 et seq. The coupling sheath 103 of the dissecting tool assembly 136 removably fits over the distal end of the incising shaft 132. The implantation site 137 is cleaned and sterilized and the needle tip 102 is inserted subcutaneously. The needle tip 102 and cutting blades on the dissecting tool assembly 136 form a progressively larger opening as the subcutaneous implantation instrument 130 is pressed downward through the skin The plunger assembly 133 is then pressed distally to inject a local anesthetic agent into the subcutaneous implantation site.

Referring next to FIG. 19, the dissecting tool assembly 136 is withdrawn from the implantation site 137 and removed from the incising shaft 132, thereby exposing the cutting edge of the incising shaft 132. The bare incising shaft 132 is inserted into the previously cleared implantation site 137 and pressed downward. Depending upon the configuration of the cutting edges 105 of the dissecting tool assembly 136, the cutting edge of the incising shaft 132 may only need to enlarge the opening, rather than clearing a full width opening.

Referring finally to FIG. 20, downward movement of the subcutaneous implantation instrument 130 is stopped when the appropriate depth for implantation has been reached and, if necessary, is urged slight back to clear the incising shaft 137 from the actual subcutaneous implantation site. The plunger assembly 133 is again pressed distally to deploy the implantable object 134 into the incising shaft 134 and thence to insert the implantable object 134 into the subcutaneous implantation site. The incising shaft 132 is withdrawn and the wound is appropriately dressed to complete the implantation procedure. Through use of the method, the subcutaneous sensor insertion of implantable objects and devices, such as sensors, having non-conforming shapes is thereby reduced to be the functional equivalent of an injection.

A cover over the distal bore opening of the implantation instrument can aid in subcutaneous device implantation while reducing trauma to tissue adjacent to the implantation site. The cover prevents coring of surrounding tissue that may occur from exposed edges when using an open bore. The cover can reduce or prevent bruising or tearing of skin during dissection by shielding blunt edges from contact with tissue. Moreover, the cover can provide additional retraction of the incision, as further described below with reference to FIGS. 24A-C.

The cover redefines the front profile of the implantation instrument. FIG. 21 is a perspective view of an implantation instrument 140 with a covered bore, in accordance with a further embodiment. The cover 142 is attached to, or otherwise extends from the top of the incising body 141 downwardly over the bore opening. The cover 142 ordinarily remains closed to conceal the distal bore opening, unless pushed open by an object, either the implant or plunger, from within the incising body 141.

The cover 142 extends from the top surface of the incising body 141 and above the top of the bore downwards towards a cutting edge 13. The bottom edge of the cover 142 swings freely and does not interfere with the cutting edge 13 when open or closed. When closed, the cover 142 sits proximal to the cutting edge 13 and opens clear of the cutting edge 13. The cover 142 attaches to the incising body 141 through an attachment assembly 143 that imparts pivotable upwards movement of the cover using a hinge, one or more pins, a joint, one or more straps, flexible adhesive, or other attachment means. In a further embodiment, the cover 142 is unitarily constructed as an extension of the top surface of the incising body 141. A crease or indentation in the top of the incising body 141, adjacent to the cover 142, allows the cover 142 to pivot away from the bore opening. Other attachment assemblies are possible.

When pivoted away from the incising body 141, the cover 142 reveals the bore opening. For example, during implantation, the cover 142 can be urged opened through pressure applied to a plunger 16 through a plunger shaft 17, by distal movement of the implantable device, or, optionally, through distal pressure on a trocar as described further below beginning with reference to FIG. 23.

At a minimum, the cover 142 is slightly larger than the distal bore opening. To ensure the front face of the instrument is smooth, the cover 142 can be as large as the outer perimeter of the distal end of the incising body 141. The overlap between the edges of the cover and the bore opening prevents the cover 142 from moving, or being pushed, inward into the bore opening under force of the surrounding tissue during use. The dermis and other tissue along the implantation axis are instead guided over the cover 142, preventing coring and tissue damage. The bottom surface of the cover 142 conformably follows the shape of the distal end of the incising body 141 to securely and completely cover the distal bore opening.

In one embodiment, the cover remains closed from the angle that the cover is attached. The weight of the door keeps the cover 142 closed against the distal end of the incising body 141 as the angle of the cover 142 follows the angle between a top edge and a bottom edge of the distal end of the incising body 141. In a further embodiment, the angle of the cover is at least equal to the angle of insertion of the incising body during incision and implantation of the implantable device, as discussed further below with reference to FIG. 22. In a further embodiment, the attachment assembly 143 provides force or tension, such as through a spring or use of elastic materials, to keep the door in closed unless pushed open by an object from within the incising body.

In one embodiment, the incising body 141 consists of an incising shaft 11 and a syringe body 15 joined together, as described above with reference to FIG. 1. In a further embodiment, the incising body 141 is unitarily constructed (not shown). The incising shaft 11 and syringe body 15 together define a continuous coaxial non-circular bore extending along a shared longitudinal axis from a proximal end of the syringe body 15 through a bore opening on the distal end of the incising shaft 11, as described above with reference to FIGS. 5A-D. In one embodiment, the bore has approximate cross-sectional dimensions less than 10 mm by 5 mm; however, other dimensions are possible, depending on implant size. In a further embodiment, the bore can vary in cross-sectional dimensions, as further described below with reference to FIG. 25.

As described above with reference to FIG. 1, the incising shaft 11 is a hollow point chisel that is formed with a beveled and rounded tip 12 that tapers into a surgically sharpened beveled cutting edge 13 formed on the distal edge. The beveled tip 12 includes a distal bore opening through which the implantable object is delivered into the implantation site. The cutting edge 13 can be formed to conformably follow an inside contour of the bore and to longitudinally taper into a sharpened straight cutting edge on a distal bottom edge of the incising shaft 11. In one embodiment, the cutting edge has rounded ends on each side that curve inwardly. The straight cutting edge 13 with rounded ends can help prevent coring or tearing of skin and flesh during implantation. Other shapes and configurations of the cutting edge are possible.

A plunger assembly includes a plunger 16, an interconnecting plunger shaft 17 and a plunger end piece 18. The plunger 16 is conformably shaped to fit within the incising body bore. The plunger end piece 18 facilitates deployment of the plunger assembly through the incising body bore and is preferably shaped to fit a thumb or palm impression. In a further embodiment, the non-circular hollow bore opens to the distal end of the incising shaft 11 and extends only partly through to form a cavity, rather than a tube, but with provision for the sliding of the plunger shaft 17, as described further below with reference to FIG. 25.

In the described embodiment, the implantation instrument 140 is designed for inexpensive and disposable use utilizing low-cost, biocompatible, and sterilizable materials. The implantation instrument 140 can be used for out-patient or non-surgical subcutaneous implant and insertion of an implantable object, as described above with reference to FIG. 18. In a further embodiment, the implantation instrument 10 is designed for single use in a prepackaged sterilized container that contains the implantable device preloaded into the implantation instrument 140. In a still further embodiment, the implantation instrument 140 is designed for reuse and can be reloaded and sterilized between implantations.

The incising body 141 can be constructed from surgical grade stainless steel or from a biocompatible plastic, such as polyetherehterketone with a stainless steel cutting edge, and has the dimensions of approximately 10 mm by 5 mm in cross section. The incising body 141 is approximately 100 mm long and the length can be varied to accommodate different implantation depths. The cover is constructed from stainless steel or a biocompatible plastic. The plunger 16 is formed from plastic and rubber and has the dimensions of approximately 8 mm by 3 mm in cross section. The plunger shaft 17 and plunger end piece 18 are formed from plastic or similar material. Other materials are possible.

Figure 22:
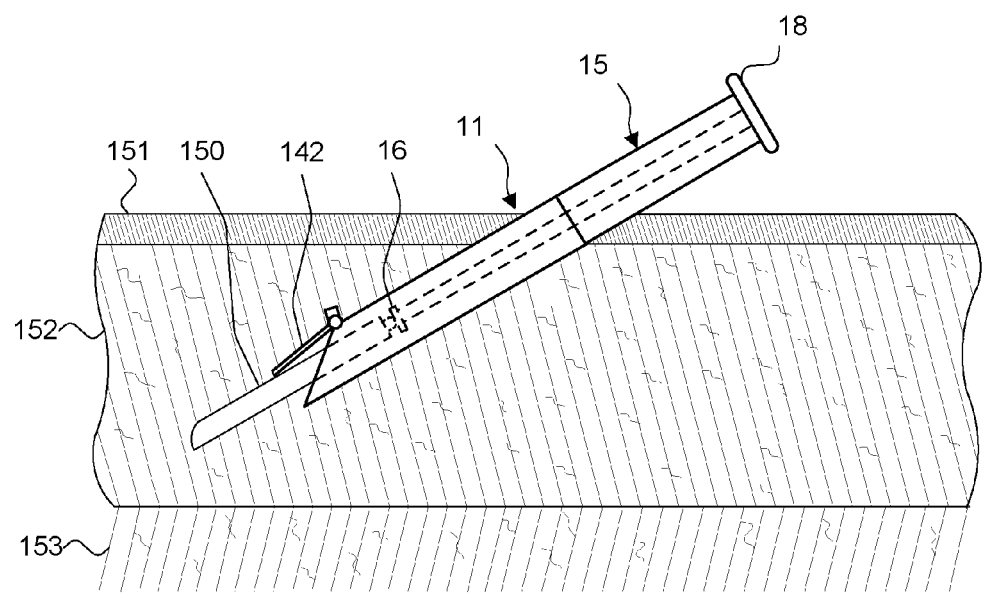
FIG. 22 is a diagrammatic view illustrating the implantation of an implantable device using the implantation instrument with a covered bore described in FIG. 21.

An implantation instrument with a covered bore can reduce the risk of injury to tissue during implant site dissection and guidance of the instrument to the implantation site. FIG. 22 is a diagrammatic view illustrating the implantation of an implantable device 150 using the implantation instrument 140 with a covered bore as described above with reference to FIG. 21. During implantation, the incising shaft 11 dissects an opening through the dermis 151 at a selected angle and is guided through the layer of subcutaneous fat 152, above the layer of muscle 153, to a subcutaneous implantation site. Absent distal force applied from within the bore, such as pushing the implantable device 150 outwards, the cover 142 remains closed during the insertion and guidance of the implantation instrument 140 to the implantation site. The implantable device 150 can be inserted through the proximal bore opening at any point or received through the distal bore opening of the incising body 141 prior to implantation. The implantable device 150 is then advanced through the distal bore opening by pushing the plunger 16 towards the subcutaneous site, thereby pivoting the cover 142 upward and away from the bore opening. The cover 142 retracts tissue surrounding the distal bore opening when pushed open in situ, aiding in decreasing risk of tissue tearing or bruising during implantation. In further embodiments, when a clearing trocar or pushing stylet of a plunger (not shown), as described above with reference to FIGS. 4A-B is employed, the plunger 16 is withdrawn from the implantation site as the cover 142 closes.

Ordinarily, the cover remains closed unless pushed open by an object pressing outward from the distal bore opening. FIG.

23A is a side view of an implantation instrument 160 with a curved cover 161 in a closed position, in accordance with a further embodiment. The bottom surface of the cover 161 matches the concave shape of the distal end of the incising body 167. The cover 161 is pivotally attached to the top surface of the distal end of the incising body 167 by an attachment assembly, such as a hinge 162. Other attachment assemblies are possible. The hinge 162 allows the cover 161 to pivot upward and away from the incising body 167 during use, as further described below beginning with reference to FIG. 24.

In a further embodiment, a stop 163 that serves as a penetration limiting mechanism extends from the top of the distal end of the incising body 167 adjacent to or as part of the hinge 162. The stop 163 can be unitarily constructed as part of the hinge 162 or fixedly or removably attached as a separate component. Other penetration limiting mechanisms are possible, such as described above with reference to FIGS. 8A-9. The stop 163 limits the depth of tissue penetration of the incising body 167. The instrument is prevented from further penetration when the stop 163 encounters the body's surface.

Figure 24A:
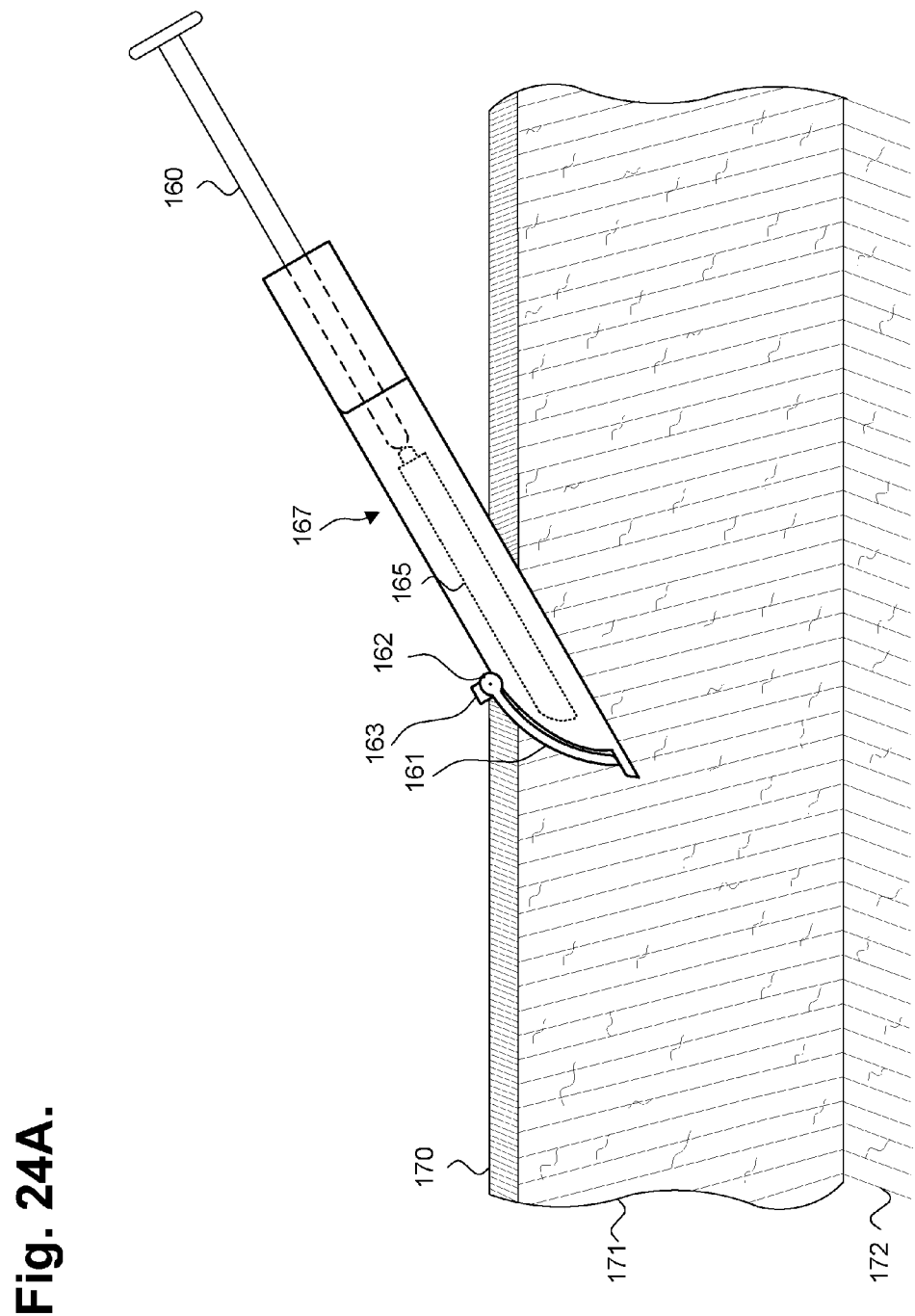
FIG. 24A is a diagrammatic view illustrating the opening into a subcutaneous site using the implantation instrument of FIGS. 23A-B.

In a further embodiment, a sharpened cutting edge 164 extends from the bottom surface of the distal end of the incising body 167 beyond the distal bore opening, such as described above with reference to FIGS. 10A-C and further below with reference to FIG. 24A. The cutting edge 164 facilitates subcutaneous implanting of the implantable device.

The plunger 165 and plunger shaft 166 are sized to fit within the bore. In one embodiment the bore is continuous in size throughout the entire length of the incising body 167, so that the plunger can be slidably moved within the incising body 167, as described above with reference to FIG. 1. In a further embodiment, the proximal bore opening is sized smaller than the working end of the plunger and the working end is received in a cavity formed on the distal end of the incising shaft. When proximally fed into the cavity from the distal end, the plunger 165 is captively held in the incising body, as further described below with reference to FIG. 25.

The cover is pushed open by an object pressing outward from the distal bore opening. FIG. 23B is a side view of the implantation instrument of FIG. 23A with the cover 161 in an open position. The plunger assembly is deployed during implantation by pushing on the plunger end piece 168 towards the implantation site, which distally slides the plunger 165 through the bore of the incising body 167. As the plunger assembly is deployed, the plunger 165 initially contacts the nearest proximal end of the implantable device 169. As the assembly is further pressed, the implantable device 169 distally moves through the opening of the bore. The implantable device 169 and plunger 165 progressively open the cover. Once the implant is placed, pressure from the surrounding tissue forces the cover back closed with only a small opening remaining due to the plunger 165 sitting under the bottom edge of the cover 161. The plunger 165 is then pulled out of the implantation site and the cover 161 returns to a fully closed position.

An implantation instrument with a covered bore can provide for sterile insertion of an implantable device. FIG. 24A is a diagrammatic view illustrating the opening into a subcutaneous site using the implantation instrument of FIGS. 23A-B. An incision site is located on the dermis 170 of a patient. The incision site is prepared for insertion of the implantation instrument 160, such as by applying lidocaine or other drugs, including anesthetic and antiarrhythmic drugs to the dermis 170. An implantable device 169 is inserted into the bore of the incising body 167 or alternatively, the implantable device 169 is prepackaged within the incising body 167. The implantable device 169 is positioned in the bore of the incising body 167 adjacent to the distal end of the plunger 165. Prior to implantation, the plunger assembly is fully retracted, so that the plunger 165 and implantable device 169 are fully located within the bore.

The implantation instrument 160 is positioned at the incision site at a selected angle and an incision is dissected in the dermis 170 under pressure applied to the instrument, which is then through the subcutaneous fat layer 171, as described above with reference to FIG. 3. As the instrument is pushed into the body, tissue surrounding the incision slides over the cover 161, preventing coring, tearing, or other damage. In a further embodiment, a stop 163 limits the depth of penetration of the instrument.

Figure 24B:
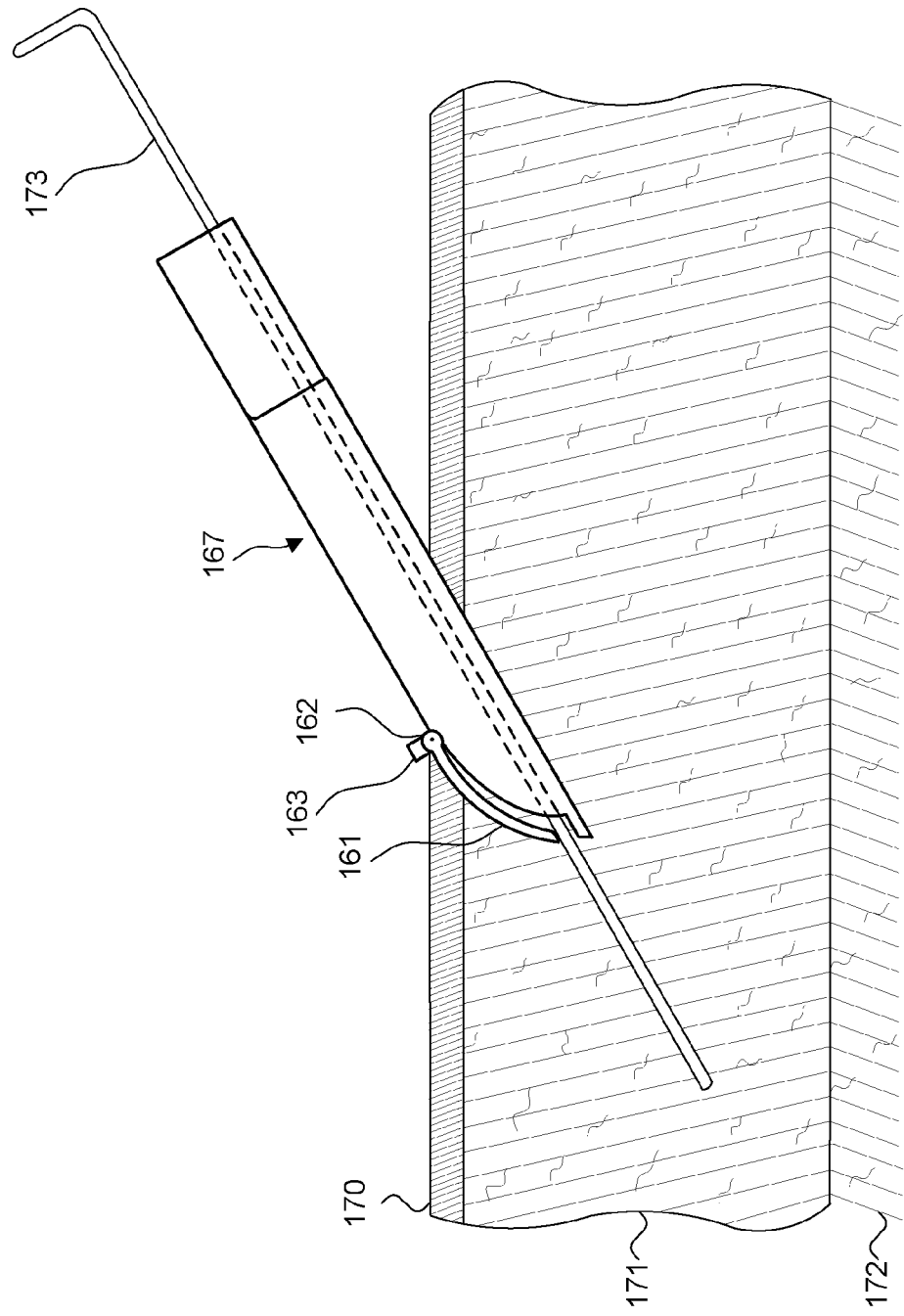
FIG. 24B is a diagrammatic view illustrating the clearing of a subcutaneous site using an implantation instrument fitted with a trocar in accordance with a further embodiment.

A trocar 173 can be optionally utilized to clear or "tunnel" a cavity in front of the tip of the incising shaft. FIG. 24B is a diagrammatic view illustrating the clearing of a subcutaneous site using an implantation instrument 160 fitted with a trocar 173 in accordance with a further embodiment. The trocar 173 has a sharpened cutting tip for clearing a subcutaneous site prior to implantation of the implantation device 169, as described above with reference to FIGS. 4A and 6. The trocar 173 is slidably received into the incising body 167 through the proximal bore opening. The trocar 173 is pushed through the incising body 167, thereby partially opening the cover 161, into the subcutaneous fat layer 171. The trocar 173 clears or "tunnels" a pathway or cavity in front of the tip of the incising shaft for receiving the implantable device. The trocar 173 is then retracted from the site and removed from of the incising body 167, wherein the cover 161 returns to a fully closed position.

Figure 24C:
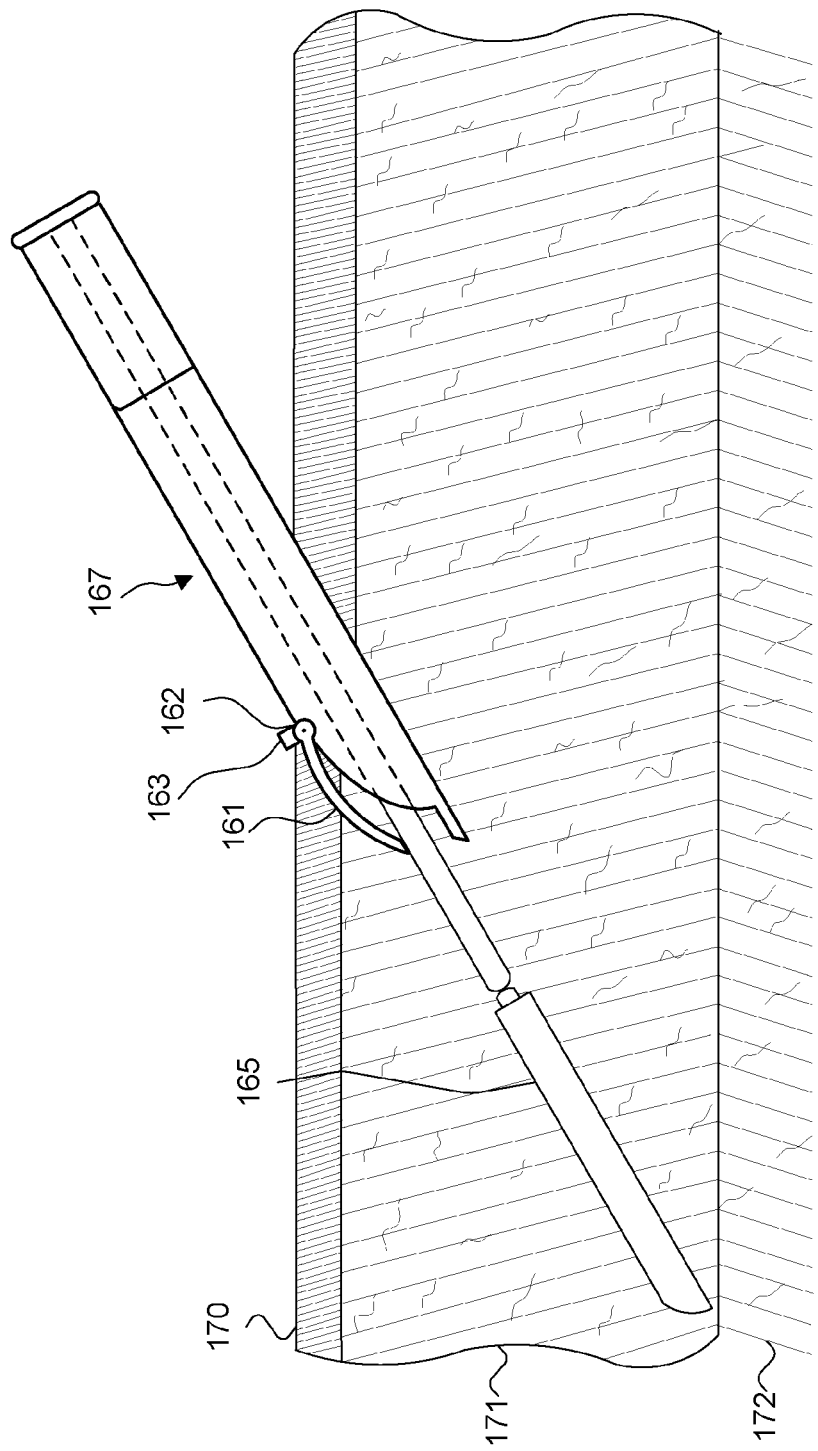
FIG. 24C is a diagrammatic view illustrating the subcutaneous implantation of an implantable device using a plunger assembly.

The implantable device 160 can be placed through the instrument into the subcutaneous fat layer 171 using a plunger assembly. FIG. 24C is a diagrammatic view illustrating the subcutaneous implantation of an implantable device 169 using a plunger assembly. The plunger assembly is deployed by pushing on the plunger end piece distally toward the implantation site, which slides the plunger assembly through the continuous bore of the incising body 167. As the plunger assembly slides along the bore, the plunger 165 contacts the implantable device 169 and slides the implantable device 169 through the bore opening, thereby opening the cover 161. If the optional trocar 173 was used, the implantable device 169 slides into the cavity formed by the trocar 173. Once the plunger assembly is retracted, the cover 161 returns to a fully closed position and the implantation instrument 160 can then be removed from the patient.

Figure 25:
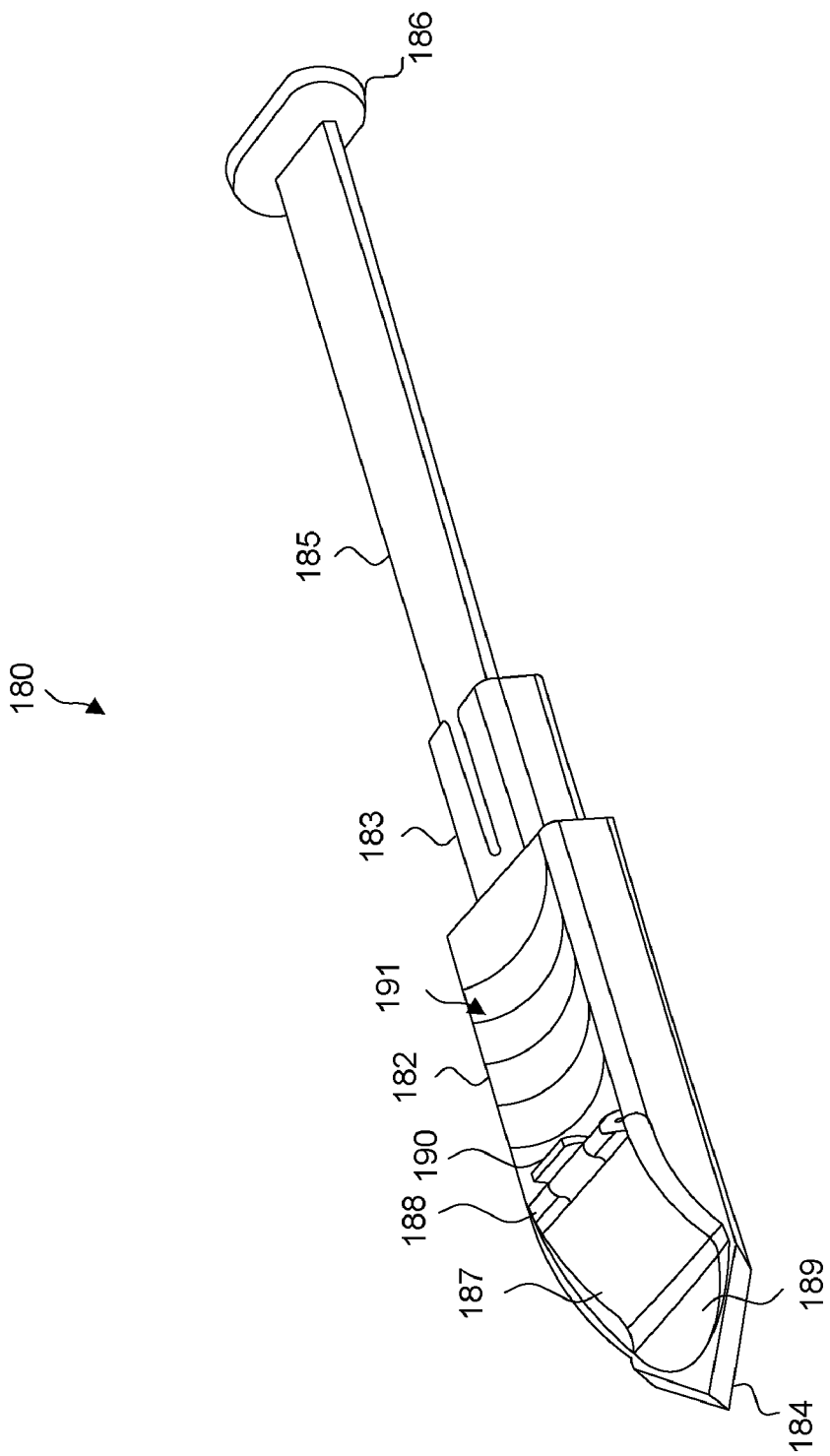
FIG. 25 is a perspective view of an implantation instrument with a lipped cover in accordance with a further embodiment.

During implantation, surrounding tissue may partially push open the cover prior to the incising body reaching the implantation site. Pressure from the surrounding tissue encountered during the incision can push against the bottom of the cover and force the cover at least partially open, which can lead to possible coring or tearing of the tissue. A cover flush with the cutting edge can reduce this premature opening. FIG. 25 is a perspective view of an implantation instrument 180 with a lipped cover in accordance with a further embodiment. The implantation instrument 180 includes an incising body 181 formed by an incising shaft 182, which is fixedly attached on one end to a syringe body 183. In a further embodiment, the incising body 181 is uniformly constructed as one component. A pointed cutting edge 184 is formed on the bottom of the distal end of the incising shaft 182, such as described above with reference to FIG. 23A.

A hollow non-circular cavity is formed within the incising shaft 182, which ends at a bore opening (not shown) proximate to the pointed cutting edge 184. The cavity is sized to receive and house an implantable device for implantation into a patient. The syringe body 183 includes a coaxial non-circular hollow bore, which can be the same height as the cavity, but have a shorter width. The smaller bore of the syringe body 183 provides support to the plunger shaft 185 while the cavity in the incising shaft 182 provides a larger interior area for the implantable device.

In a further embodiment, the cavity and the bore are non-circular. The incising shaft 182 and the syringe body 183 are positioned end-to-end, so that one end of the syringe body 183 is centered on an end of the incising shaft 182 to align a portion of the cavity of the incising shaft 182 with the bore of the syringe body 183. An opening extends from one end of the incising body continuously through an opposite end on the syringe body. In one embodiment, the dimensions of the incising shaft 182 are approximately 13 mm×25 mm×40 mm, while the dimensions of the syringe body 183 are approximately 13 nm×28 nm×24 nm. In a further embodiment, the height of the syringe body 183 can also be shorter than the height of the incising shaft 182.

The incising shaft 182 is affixed to the syringe body 183 such that the syringe body 183 is centered on the proximal end of the incising shaft 182 and the bore is aligned with a portion of the cavity. The incising body 181 houses a plunger (not shown). The plunger is attached to a plunger shaft 185 and plunger end piece 186, forming a plunger assembly. In one embodiment, the bore of the syringe body 183 is sized so that the plunger is slidably removable from the incising body 181. In a further embodiment, the plunger is sized larger that the bore size of the syringe body 183 so that the plunger is captively held within the incising shaft 182 cavity while the plunger shaft 185 is sized to slide within the syringe body 183 bore. In a still further embodiment, a containment edge (not shown) can be formed around a periphery of the plunger to prevent removal of the plunger assembly from the incising body 181.

A cover 187 is affixed to, or otherwise extends from, the top surface of the incising shaft 182 on a distal end, via an attachment assembly 188, as discussed above with reference to FIG. 21. The cover 187 is sized and shaped to cover the bore opening. The cover 187 prevents coring of surrounding tissue and tearing of skin that can occur during incision by the cutting edge of the implantation instrument. The cover 187 also provides additional retraction of the incision during the subcutaneous implantation of an implantable object.

A lip 189 extends outward in a rounded shape from the distal end of the cover 187 and is angled coplanar to a top surface of the cutting edge 184. The cutting edge 184 has a margin with a recessed region on the top surface sized to receive the lip 189. When the cover 187 is closed, the top surface of the lip 189 is flush with the top surface of the cutting edge 184. In a further embodiment, the top surface of the lip 189 can sit below the top surface of the cutting edge 184. The lip 189 and recess reduce the risk of the dermis or other tissue from pushing the cover 187 open during incision and implantation.

In a further embodiment, a stop 190 serves as a penetration limitation mechanism 190 that can be affixed to the top surface of the incising shaft adjacent to or part of the attachment assembly 188. The stop 190 extends away from the incising shaft 182 to form a barrier that prevents insertion of the implantation instrument 180 beyond the stop 190. The stop 190 can be formed as part of the cover attachment assembly 188 or separate from the attachment assembly 188.

In a still further embodiment, one or more notches 191 are formed on at least one external surface of the incising body 181. The notches 191 aid in gripping the incising body 181 during incision of the dermis and implantation of the implantable device. Notches 191 can extend outward from or inward into the surface of the incising body. For example, notches can be indentations, ridges, nodules, or divots. Other types of notches 191 are possible.

While the invention has been particularly shown and described as referenced to the embodiments thereof, those skilled in the art will understand that the foregoing and other changes in form and detail may be made therein without departing from the spirit and scope of the invention.

What is claimed is:

1. An instrument for use in subcutaneous implantation, comprising:
    an incising body comprising:
        an incising shaft open on both distal and proximal ends with a non-circular bore being defined along a longitudinal axis, the bore of the incising shaft sized to enclose an implant, the incising shaft comprising a distal end having a beveled surface transversely formed beginning on a top surface and ending on a bottom surface that has a sharpened bottom edge; and
        a syringe body open on both distal and proximal ends with a non-circular bore being defined along a longitudinal axis, the bore of the syringe body also sized to enclose the implant, the syringe body being fixedly attached to a proximal end of the incising shaft;
    a solid cover sized to cover the open distal end of the incising shaft, the solid cover pivotably attached to the top surface of the distal end of the incising shaft and extending down to the bottom edge of the distal end of the incising shaft, the solid cover disposed to remain closed absent distal force applied from within the bore of the incising shaft; and
    a plunger slideably contained within the bores of the incising shaft and the syringe body.

2. An instrument according to claim 1, further comprising:
    a tensioner configured to apply downward force to the solid cover and disposed to resist the distal force applied to the solid cover from within the bore of the incising shaft.

3. An instrument according to claim 1, wherein the solid cover pivots on at least one of a hinge, and a pin provided on the distal end of the top edge of the incising shaft.

4. An instrument according to claim 1, wherein the solid cover comprises one of a flat, concave, and convex side profile.

5. An instrument according to claim 1, further comprising:
    a stop extending upwards from the top surface of the distal end of the incising body and adjacent to a proximal end of the solid cover.

6. An instrument according to claim 1, further comprising:
    one or more notches on at least one outer surface of the incising body.

7. An instrument for use in subcutaneous implantation, comprising:
    an incising body comprising:
        an incising shaft open on both distal and proximal ends with a non-circular bore being defined along a longitudinal axis, the bore of the incising shaft sized to enclose an implant, the incising shaft comprising a distal end having a beveled surface transversely formed beginning on a top surface and ending on a bottom surface that has a sharpened bottom edge;
        a solid cover formed as an integral extension of the top surface of the distal end of the incising shaft, the solid cover extending down to the bottom edge of the distal end of the incising shaft and sized to cover the open distal end of the incising shaft, the solid cover disposed to pivot on a crease transversely formed in the top surface and remain closed absent distal force applied from within the bore of the incising shaft; and a syringe body open on both distal and proximal ends with a non-circular bore being defined along a longitudinal axis, the bore of the syringe body also sized to enclose the implant, the syringe body being fixedly attached to a proximal end of the incising shaft; and a plunger slideably contained within the bores of the incising shaft and the syringe body.

8. An instrument according to claim 7, wherein the solid cover comprises one of a flat, concave, and convex side profile.

9. An instrument according to claim 7, further comprising:
a stop extending upwards from the top surface of the distal end of the incising body and adjacent to a proximal end of the solid cover.

10. An instrument according to claim 7, further comprising:
one or more notches on at least one outer surface of the incising body.

11. An instrument for use in subcutaneous implantation, comprising:
an incising body, comprising:
an incising shaft defining a cavity along a longitudinal axis of the incising shaft and open on a distal end and partially open on a proximal end, the incising shaft comprising a distal end having a beveled surface transversely formed beginning on a top surface and ending on a bottom surface that has a sharpened bottom edge, the cavity sized to enclose an implant; and
a syringe body defining a bore that is shorter than the incising shaft in length and narrower than both the cavity and the incising shaft in width and height along a longitudinal axis of the syringe body and open on both distal and proximal ends, a distal end of the syringe body being affixed to a proximal end of the incising shaft with the bore aligned with the partially open proximal end of the cavity;
a plunger comprising a horizontal flat surface sized to fit within a width of the cavity, the plunger being affixed to a distal end of a plunger shaft that is sized to slide longitudinally within the bore of the incising shaft; and
a solid cover sized to cover the open distal end of the incising shaft, the solid cover pivotably attached to a top edge of the distal end of the incising shaft and extending down to the bottom edge of the distal end of the incising shaft, the solid cover disposed to remain closed absent distal force applied from within the cavity.

12. An instrument according to claim 11, further comprising:
a stop extending upwards from the top surface of the distal end of the incising body and adjacent to a proximal end of the solid cover.

13. An instrument according to claim 11, wherein the solid cover comprises one of a flat, concave, and convex side profile.

14. An instrument for use in subcutaneous implantation, comprising:
an incising body, comprising:
an incising shaft defining a cavity along a longitudinal axis of the incising shaft and cavity along a longitudinal axis of the incising shaft and open on a distal end and partially open on a proximal end, the incising shaft comprising a distal end having a beveled surface transversely formed beginning on a top surface and ending on a bottom surface, a pointed cutting edge formed as an integral extension of the bottom surface of the distal end of the incising shaft has a sharpened bottom edge and a recess defined on the top surface of the pointed cutting edge, the cavity sized to enclose an implant; and
a syringe body defining a bore that is shorter than the incising shaft in length and narrower than both the cavity and the incising shaft in width and height along a longitudinal axis of the syringe body and open on both distal and proximal ends, a distal end of the syringe body being affixed to a proximal end of the incising shaft with the bore aligned with the partially open proximal end of the cavity;
a plunger comprising a horizontal flat surface sized to fit within a width of the cavity, the plunger being affixed to a distal end of a plunger shaft that is sized to slide longitudinally within the bore of the incising shaft; and
a solid cover sized to cover the open distal end of the incising shaft, the solid cover disposed to remain closed absent distal force applied from within the cavity, the solid cover pivotably attached to a top edge of the distal end of the incising shaft and extending down to the bottom edge of the distal end of the incising shaft, the solid cover further comprising a lip extending from the distal edge of the solid cover, the lip angled coplanar to the top surface of the pointed cutting edge and shaped to conformably fit within the recess, the lip disposed to maintain a seal between the open distal end of the incising shaft and the recess.

15. An instrument according to claim 14, further comprising:
a stop extending upwards from the top surface of the distal end of the incising body and adjacent to a proximal end of the solid cover.

16. An instrument according to claim 14, further comprising:
one or more notches on at least one outer surface of the incising body.

17. An instrument according to claim 14, wherein the solid cover comprises one of a flat, concave, and convex side profile.

18. An instrument according to claim 11, further comprising:
one or more notches on at least one outer surface of the incising body.

\* \* \* \* \*